(12) United States Patent
Joseph et al.

(10) Patent No.: US 11,896,730 B1
(45) Date of Patent: Feb. 13, 2024

(54) REPROCESSING A SINGLE-USE MEDICAL DEVICE

(71) Applicant: INNOVATIVE HEALTH, Scottsdale, AZ (US)

(72) Inventors: Blessan C. Joseph, Chandler, AZ (US); Rafal Chudzik, Peoria, AZ (US); Haley C. Ellis, Marana, AZ (US)

(73) Assignee: INNOVATIVE HEALTH, Scottsdale, AZ (US)

( * ) Notice: Subject to any disclaimer, the term of this patent is extended or adjusted under 35 U.S.C. 154(b) by 0 days.

(21) Appl. No.: 18/491,553

(22) Filed: Oct. 20, 2023

Related U.S. Application Data

(60) Provisional application No. 63/380,266, filed on Oct. 20, 2022.

(51) Int. Cl.
*A61L 2/18* (2006.01)
*B08B 3/08* (2006.01)
*B08B 7/02* (2006.01)
*B08B 7/04* (2006.01)
*B08B 1/00* (2006.01)

(52) U.S. Cl.
CPC .............. *A61L 2/186* (2013.01); *B08B 1/006* (2013.01); *B08B 3/08* (2013.01); *B08B 7/028* (2013.01); *B08B 7/04* (2013.01); *A61L 2202/17* (2013.01); *A61L 2202/24* (2013.01)

(58) Field of Classification Search
CPC .. A61L 2/186; A61L 2202/17; A61L 2202/24; B08B 1/006; B08B 3/08; B08B 7/028; B08B 7/04
See application file for complete search history.

(56) References Cited

U.S. PATENT DOCUMENTS

| | | | | |
|---|---|---|---|---|
| 11,786,620 B2 * | 10/2023 | Paul | ......................... | A61L 2/24 422/3 |
| 2005/0011538 A1 * | 1/2005 | Nordquist | .............. | A61B 50/36 134/25.1 |
| 2005/0029142 A1 * | 2/2005 | Nordquist | .............. | A61B 50/36 206/438 |
| 2011/0270179 A1 * | 11/2011 | Ouyang | ............. | A61B 1/00062 604/110 |
| 2017/0215699 A1 * | 8/2017 | Ouyang | ............. | A61B 1/00045 |
| 2022/0273837 A1 * | 9/2022 | Paul | ....................... | A61L 2/085 |
| 2023/0240794 A1 * | 8/2023 | Johnson | ................ | A61B 90/70 134/198 |

FOREIGN PATENT DOCUMENTS

| | | | | |
|---|---|---|---|---|
| CA | 3017004 A1 * | 3/2019 | ......... | A61B 1/00057 |
| WO | WO-2008034913 A2 * | 3/2008 | ......... | A61B 5/04842 |
| WO | WO-2020086302 A1 * | 4/2020 | ........... | A61L 29/005 |

OTHER PUBLICATIONS

CN 115192869 (Year: 2022).*

(Continued)

*Primary Examiner* — Alexander Markoff
(74) *Attorney, Agent, or Firm* — POLSINELLI PC

(57) ABSTRACT

The present invention provides a method for reprocessing single-use medical devices. The method can include removing a coating from a single-use medical device, validating the removal of the coating, cleaning the single-use medical device, and applying a new coating to the single-use medical device.

20 Claims, 12 Drawing Sheets

(56) References Cited

OTHER PUBLICATIONS

CN 113797399 (Year: 2021).*
CN 105412995 (Year: 2016).*
Frequently-Asked-Questions. FDA (Year: 2001).*
Three Additional Questions. FDA (Year: 2003).*
The Safety of Reprocessed Medical Devices Marketed for Single-Use. SCENIHR (Year: 2010).*
BR 102018067579 (Year: 2019).*

* cited by examiner and reduces tissue irritation and damage. Yet, these coatings can also trap biological contaminants and are difficult to detect and remove during a reprocessing method.

What is needed is a reprocessing method which clearly detects the coating(s), removes of the coating(s), validates of the removal of the coating(s), cleans the surface of the single-use medical device after the coating is removed, applies a new coating, and validates the new coating on the single-use medical device.

REPROCESSING A SINGLE-USE MEDICAL DEVICE

CROSS-REFERENCE TO RELATED APPLICATIONS

This application claims the benefit under 35 U.S.C. § 119(e) to U.S. Provisional Application No. 63/380,266, filed Oct. 20, 2022, the entire contents of which are incorporated herein by reference in their entirety.

FIELD OF THE INVENTION

The present disclosure generally relates to methods of reprocessing a single-use medical device.

BACKGROUND OF THE INVENTION

Medical devices are used widely in the health-care facility. These medical devices can be categorized into two general groups: reusable medical devices and single-use medical devices. Reusable medical devices like endoscopes, forceps and stethoscopes can be reprocessed and quickly returned to service. Depending on the classification of the device, the reusable medical device may be reprocessed and include point-of-use treatment, cleaning, packaging, high level disinfection and sterilization, among other steps. Following industry and governmental guidelines as well as best practices for reusable medical device reprocessing, these guideline helps to reduce the risk of infection and improve patient outcomes in a healthcare facility.

To ensure patient and staff safety as well as staying compliant, reprocessing medical devices is a necessary practice when the device or instrument is reusable. Reprocessing a single-use medical device can offer economic benefits for the healthcare facility and patent, as the alternative is purchasing disposable instruments or devices for use during only a single patient procedure. While other costs are associated with medical device reprocessing (device repair and replacement, cleaning chemistries, capital purchases like sinks, washer/disinfectors, sterilizers, etc.), reprocessing a single-use medical device through a third party or within the hospital has economic benefits for the facility.

Ensuring the facility is following regulations and guidelines from governing bodies such as the Association for the Advancement of Medical Instrumentation (AAMI) is vital to promoting patient and staff safety and remaining complaint. More importantly, each step of the reprocessing cycle must be done carefully and thoroughly to reduce the risk of patient infection (Healthcare-Associated Infection) or injury. Each step in the reprocessing cycle must be validated.

Single-use medical devices such as Class II and Class III medical devices can also be reprocessed. Class II and Class III single use medical devices such as electrophysiology catheters, and cardiac catheterization catheters, are frequently used in the health-care industry. For single-use medical device, the reprocessing protocol is necessary to ensure the single-use medical device is properly cleaned to remove visible soil, non-visible soil, biological contaminates (such as dried blood), and sterilized. Yet, the single-use medical devices have a coating which provides these single-use medical devices with a lubricous coating. These lubricous coatings enable the physician to reach more distal regions and to cross difficult lesions; reduced procedure time; reduces insertion forces; increases patient comfort; enhances the ability to maneuver tortuous paths; provides more precise push and torque control; and reduces tissue irritation and damage. Yet, these coatings can also trap biological contaminants and are difficult to detect and remove during a reprocessing method.

SUMMARY OF THE INVENTION

Provided herein is a method for reprocessing a single-use medical device. The method can include removing one or more coatings on a surface of the single-use medical device, validating the surface of the single-use medical device for the coating removal, and preparing the surface of the single-use medical device to form a prepared surface on the single-use medical device. In an aspect, the method can further include detecting the one or more coatings on the surface of the single-use medical device prior to removing the one or more coatings. In another aspect, detecting the one or more coatings includes detecting a length, width, thickness, mass, geometry, and chemical composition of the one or more coatings.

In various aspects, the method can further include applying one or more new coatings on the prepared surface of the single-use medical device and validating the one or more new coatings on the single-use medical device. In an aspect, the one or more coatings is a polymeric coating. In another aspect, the polymeric coating is a single polymeric coating, two polymeric coatings, or more than two polymeric coatings. In another aspect, the polymeric coating comprises a hydrophobic polymeric coating, a hydrophilic polymeric coating, an amphiphilic coating, or a combination thereof. In an aspect, the polymer coating is a hydrophilic polymeric coating. In another aspect, the one or more coatings have a thickness from about 5.0 μm to about 250 μm.

In various aspects, validating the surface of the single-use medical device for coating removal includes detecting a presence or an absence of a residual coating on the surface of the single-use medical device. In another aspect, when the presence of the residual coating on the surface of the single-use medical device is detected the single-use medical device undergoes removing the one or more coatings for a second time. In an aspect, the method meets FDA requirements and industrial standards. In an aspect, detecting the one or more coatings on the single-use medical device comprises utilizing a light assembly, a fluid assembly, magnification, a dye assembly, an artificial intelligence method, a scanning electron microscope assembly, a differential scanning calorimetry assembly, or a combination thereof.

In various aspects, removing the one or more coatings from the single-use medical device includes utilizing a mechanical removal assembly, a chemical removal assembly, an environmental removal assembly, or a combination thereof. In an aspect, the mechanical removal assembly is an ultrasonic assembly, a high-pressure water jet assembly, a solvent wiping assembly, bead blasting assembly, laser removal assembly, or a combination thereof. In an aspect, the chemical method comprises electrostatic removal assembly, an acidic removal assembly, or a basic removal assembly. In another aspect, the environmental method comprises a heat method, a freeze method, or a vacuum method. In an aspect, preparing the surface of the single-use medical device includes cleaning the surface, rinsing the surface with a polar solvent, and drying the surface of the single-use medical device. In an aspect, the drying step is conducted from about 50 degrees C. (Celsius) to about 150 degrees C. In an aspect, removing the one or more coatings from the single-use medical device comprises exposing the one or more coatings to denatured ethyl alcohol.

Further provided herein is a method for reprocessing a single-use medical device. The method can include removing one or more coatings on a surface of the single-use medical device by contacting the one or more coatings on the surface of a single-use medical device to denatured ethyl alcohol, wherein the denatured ethyl alcohol removes the one or more coatings; validating the surface of the single-use medical device for the coating removal by visually inspecting the single-use medical device for any residual coating or using other detection methods; and preparing the surface of the single-use medical device for coating to form a prepared surface on the single-use medical device. Preparing the surface of the single-use medical device can include contacting the single-use medical device to a hydrogen peroxide solution, providing an ultrasonic frequency to the single-use medical device in the hydrogen peroxide solution, rinsing the single-use medical device with water, and drying the single-use medical device.

In various aspects, the single-use medical device is soaked in the hydrogen peroxide solution before or after the ultrasonic frequency is provided. In another aspect, the ultrasonic frequency is provided for about 5 minutes to about 30 minutes. In an aspect, contacting the one or more coatings with denatured ethyl alcohol includes wiping the one or more coatings five times with a polyester wipe containing denatured ethyl alcohol. In an aspect, contacting the one or more coatings with denatured ethyl alcohol includes soaking the single-use medical device in a tank filled with denatured ethyl alcohol for about 5 minutes to about 1 hour and then wiping the one or more coatings off the surface of the single-use medical device using a polyester wipe or rag. In an aspect, validating the surface of the single-use medical device for the coating removal further includes a light detection method, a fluid detection method, a magnification method, a dye method, an artificial intelligence method, a scanning electron microscope method, a differential scanning calorimetry method, or any combination thereof. In an aspect, the one or more coatings are hydrophilic coatings.

In some aspects, method further includes wiping a luer and a strain relief the single-use medical device with a polyester wipe containing 3% hydrogen peroxide solution. In an aspect, the water used to rinse the single-use medical device has a temperature of about 15 degrees C. to about 30 degrees C. In an aspect, drying the single-use medical device includes applying a temperature of about 50 degrees C. to about 150 degrees C. In an aspect, drying the single-use medical device includes wiping the single-use medical device 10 times with a dry polyester wipe. In another aspect, the method further includes validating the prepared surface using visual inspection to ensure the prepared surface is ready for a new coating to be applied. In an aspect, the method further includes sterilizing the single-use medical device. In another aspect, the method further includes applying one or more new coatings to the single-use medical device and validating the one or more new coatings on the single-use medical device. In another aspect, removing the one or more coatings further includes mechanically removing the one or more coatings, chemically removing the one or more coatings, environmentally removing the one or more coatings, or any combination thereof.

In various aspects, mechanically removing the one or more coatings includes an ultrasonic removal method, a high-pressure water jet removal method, a bead blasting method, a laser removal method, or a combination thereof. In an aspect, chemically removing the one or more coatings includes providing an electrostatic charge to the one or more coatings, providing an acidic solution to the one or more coatings, providing a basic solution to the one or more coatings, or combinations thereof. In an aspect, environmentally removing the one or more coatings includes heating the one or more coatings to a temperature above a melting point of the one or more coatings, cooling the one or more coatings to freeze the one or more coatings, or placing the one or more coatings in a vacuum chamber. In an aspect, the one or more coatings have a thickness of about 5.0 µm to about 250 µm. In another aspect, the single-use medical device has been used in a patient prior to removing the one or more coatings.

BRIEF DESCRIPTION OF THE FIGURES

The description will be more fully understood with reference to the following figures and graphs, which are presented as various embodiments of the disclosure and should not be construed as a complete recitation of the scope of the disclosure. It is noted that, for purposes of illustrative clarity, certain elements in various drawings may not be drawn to scale. Understanding that these drawings depict only exemplary embodiments of the disclosure and are not therefore to be considered limiting of its scope, the principles herein are described and explained with additional specificity and detail through the use of the accompanying drawings in which.

DETAILED DESCRIPTION OF THE INVENTION

Figure 1:
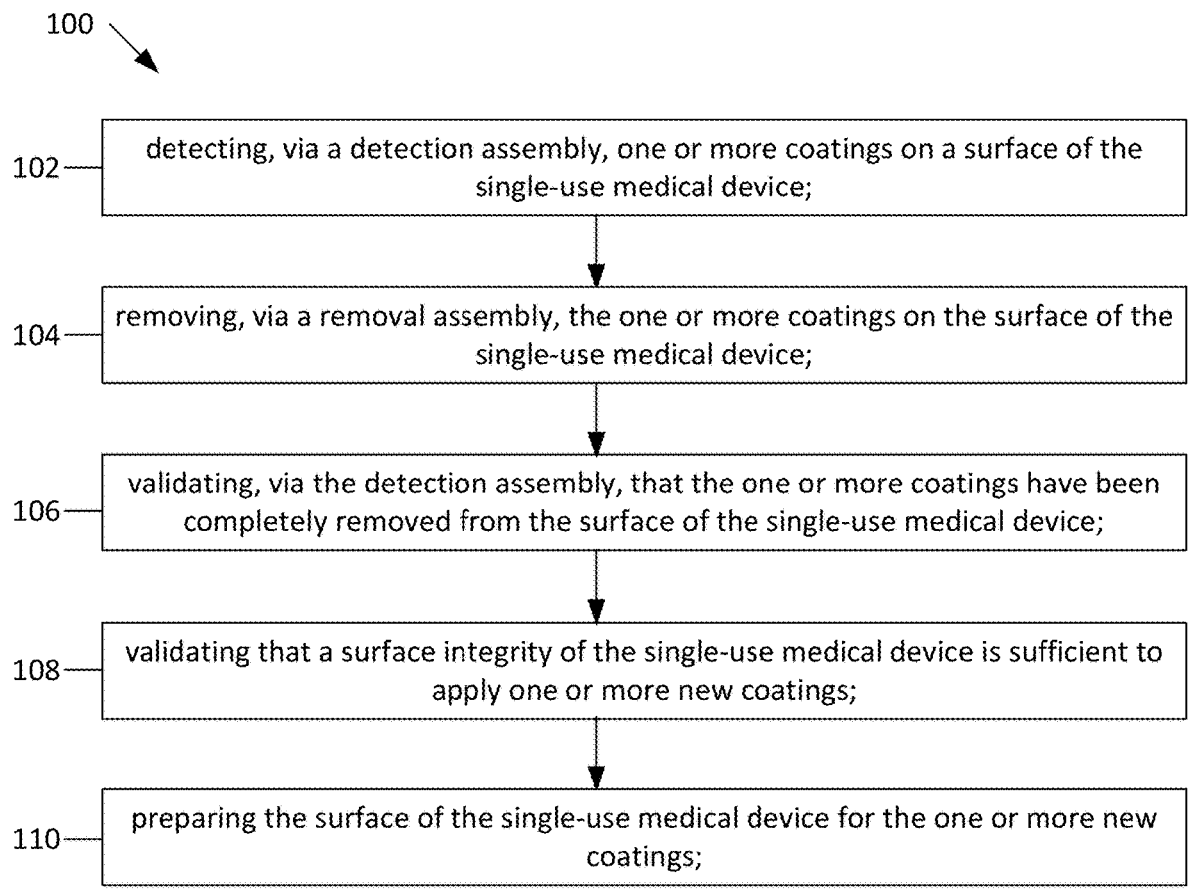
FIG. 1 is flow chart of an exemplary method in one aspect.

Various embodiments of the disclosure are discussed in detail below. While specific implementations are discussed, it should be understood that this is done for illustration purposes only. A person skilled in the relevant art will recognize that other components and configurations may be used without parting from the spirit and scope of the disclosure. Thus, the following description and drawings are illustrative and are not to be construed as limiting. Numerous specific details are described to provide a thorough understanding of the disclosure. However, in certain instances, well-known or conventional details are not described in order to avoid obscuring the description. References to one or an embodiment in the present disclosure can be references to the same embodiment or any embodiment; and such references mean at least one of the embodiments.

Reference to "one embodiment," "an embodiment," or "an aspect" means that a particular feature, structure, or characteristic described in connection with the embodiment is included in at least one embodiment of the disclosure. The appearances of the phrase "in one embodiment" or "in one aspect" in various places in the specification are not necessarily all referring to the same embodiment, nor are separate or alternative embodiments mutually exclusive of other embodiments. Moreover, various features are described which may be exhibited by some embodiments and not by others.

As used herein, "about" refers to numeric values, including whole numbers, fractions, percentages, etc., whether or not explicitly indicated. The term "about" generally refers to a range of numerical values, for instance, ±0.5-1%, ±1-5% or ±5-10% of the recited value, that one would consider equivalent to the recited value, for example, having the same function or result.

The terms used in this specification generally have their ordinary meanings in the art, within the context of the disclosure, and in the specific context where each term is used. Alternative language and synonyms may be used for any one or more of the terms discussed herein, and no special significance should be placed upon whether or not a term is elaborated or discussed herein. In some cases, synonyms for certain terms are provided. A recital of one or more synonyms does not exclude the use of other synonyms. The use of aspects anywhere in this specification including aspects of any terms discussed herein is illustrative only and is not intended to further limit the scope and meaning of the disclosure or of any example term. Likewise, the disclosure is not limited to various embodiments given in this specification.

Additional features and advantages of the disclosure will be set forth in the description which follows, and in part will be obvious from the description, or can be learned by practice of the herein disclosed principles. The features and advantages of the disclosure can be realized and obtained by means of the instruments and combinations particularly pointed out in the appended claims. These and other features of the disclosure will become more fully apparent from the following description and appended claims or can be learned by the practice of the principles set forth herein.

The present disclosure encompasses methods for reprocessing a single medical use device. The methods comprise the following steps: a) detecting a coating(s) on a surface of the single-use medical device; b) removing the coating(s) on the surface of the single-use medical device; c) validating the surface of the single-use medical device for the coating(s) removal; d) preparing the surface of the single-use medical device to form a prepared surface on the single-use medical device; e) applying a new coating on the prepared surface of the single-use medical device; and f) validating the new coating on the single use-medical device. The methods, detailed herein, would meet FDA guidelines. These methods can be used on Class II and Class III medical devices such as electrophysiology catheters, cardiac catherization catheters, and other Class I, Class II, and Class III medical devices.

In some aspects, the coating on the single-use medical device comprises a polymer coating. The polymeric coating is a single polymeric coating, two polymeric coatings, or more than two polymeric coatings. The polymers may be linear or branched. The two or more polymeric coatings are applied on the surface of the existing coating.

In an aspect, the polymeric coating can include a hydrophobic polymeric coating, a hydrophilic polymeric coating, an amphiphilic polymeric coating, or a combination thereof. In an aspect, the polymeric coating comprises a hydrophobic polymeric coating. The hydrophobic polymeric coatings comprise acrylics, epoxies, polyethylene, polystyrene, polyvinylchloride, polytetrafluorethylene, polydimethylsiloxane, polyesters, and polyurethanes. In some aspects, the polymeric coating comprises a hydrophilic polymeric coating. Hydrophilic polymeric coatings can be poly(ethylene glycol), poly(vinyl alcohol), polyglutamic acid), poly (vinyl pyrrolidone), polyacrylamide, and polyethyleneimine. In another aspect, the polymeric coating comprises an amphiphilic polymeric coating which have both polar and non-polar regions where the polymer may be a copolymer or a triblock copolymer. The amphiphilic polymeric coating comprises monomers of a polar and non-polar monomer.

In another aspect, the polymeric coating is a hydrophilic polymeric coating. The hydrophilic polymeric coating is poly(vinylpyrrolidone) or PVP. These hydrophilic polymeric coatings are polar in nature and provide hydrogen bonds with many polar functional groups such as alcohols, amines, carboxylic acids, and amides. The hydrophilic polymeric coating also adheres to the single medical-use device through ionic interaction. Since these hydrophilic polymeric coatings are polar, they readily dissolve in polar solvents such as water and alcohols (such as ethanol and iso-propanol). The one or more coatings can be liquid coatings or cured coatings. Hydrophilic coatings can bind to water or other fluids, thereby producing a lubricous surface on the coating. The lubricous surface can provide for less friction between the single-use medical device and the blood of the patient, thereby providing many significant benefits such as reducing damage to blood vessels, reducing procedure times, and reducing required torques and forces, amongst other benefits known in the art.

In some aspects, after the single-use medical device is used in a patient, the single-use medical device cannot be reused due to the hydrophilic coating having been activated. In some aspects, activation of the hydrophilic coating within the patient can cause the properties of the hydrophilic coating to change, thereby taking the hydrophilic coating outside of FDA and/or manufacturer requirements. The hydrophilic coating can expand in the blood of the patient and lose certain geometries necessary for safe use at a later procedure. The hydrophilic coating can partially dissolve thereby losing thickness, length, width, or other desired geometries. The hydrophilic coating can lose thickness, length, width, or other necessary geometries during use in a human patient and therefore may not be safe for a second use. In other aspects, hydrophilic coatings are difficult to clean and sterilize for reuse, therefore reusing a single-use medical device can cause introduction of bacterial contamination or other types of contamination into the second patient when reused.

The thickness of the one or more coatings on the single-use medical device can range from about 5.0 µm to about 250 µm, or more. In various aspects, the thickness of the one or more coatings on the single-use medical device can range from about 5.0 µm to about 250 µm, from about 5.0 µm to about 20 µm, from about 20 µm to about 40 µm, from about 40 µm to about 60 µm, from about 60 µm to about 80 µm, from about 80 µm to about 100 µm, from about 100 µm to about 125 µm, from about 125 µm to about 150 µm, from about 150 µm to about 175 µm, from about 175 µm to about 200 µm, from about 200 µm to about 225 µm, from about 225 µm to about 250 µm, or more. In one aspect, the thickness of the one or more coatings is about 40 µm. In another aspect, the thickness of the one or more coatings is about 60 µm to 80 µm.

The one or more coatings of the single-use medical device may have a geometry which is uniform or a non-uniform geometry. A "uniform" geometry generally indicates that the surface of the one or more coatings is relatively smooth and consistent. A "non-uniform" geometry relatively indicates that there are relative high points (peaks) and low points (valleys) in the one or more coatings (e.g., differing thickness throughout the length and/or width of the one or more coatings). The removal of the one or more coatings removes the one or more coatings but also maintains the surface and integrity of the single medical-use device.

In some aspects, the one or more coatings of the single-use medical device may further include a lubricant. These lubricants aid in the use of the single-use medical device. Medical lubricants can be a silicon-based lubricant, a medical grade water-based lubricant, krytox biocompatible lubricant, nyoil lubricant, WD-40, surgilube, or a medical lubricant gel.

FIG. 1 illustrates a flow chart for an exemplary method 100 for reprocessing a single-use medical device. At block 102, the method 100 can include detecting one or more coatings on a surface of the single-use medical device. Detecting the one or more coatings can include using a detection assembly to detect a number, a length, a width, a thickness, and a chemical composition of each coating on the single-use medical device. In some aspects, the detection assembly can include a light assembly, a fluid assembly (e.g., liquid or humidity assembly), a magnification assembly, a dye assembly, an AI based detection assembly, a scanning electron microscope assembly, a differential scanning calorimetry assembly, and/or visual inspection. Each of these detection assemblies are described in further detail herein.

In some aspects, the method can include soaking the single-use medical devices in a tank containing an enzymatic solution before removing the one or more coatings. The enzymatic solution can have a temperature of about 15 degrees C. to about 30 degrees C. The enzymatic solution can have 1 gallon of enzymatic solution and 5 gallons of RO water. In some aspects, a pump can be used to circulate the enzymatic solution in the tank. In some aspects, the devices can then be rinsed with RO water provided by a water nozzles at a flow rate of about 2.5 gallons/minute to about 3.5 gallons/per minute. The devices can then be visually inspected for any damage, or the detection assemblies can be used to test the devices for any damage. In some aspects, the lumens of the single-use medical device can be cleared using a lumen clearing guidewire.

At block 104, the method 100 can include removing the one or more coatings on the surface of the single-use medical device. Removing the one or more coatings on the single-use medical device can include using a removal assembly. In some aspects, the removal assembly can be a mechanical removal assembly, a chemical removal assembly, or an environmental removal assembly. The mechanical removal assembly can include one or more of an ultrasonic removal assembly, a water jet removal assembly, a wiping removal assembly, a bead blasting removal assembly, a laser removal assembly, or other mechanical removal assemblies operable to remove one or more coatings from a single-use medical device. The chemical removal assemblies can include an electrostatic charge removal assembly, an acidic removal assembly, an alkaline removal assembly, or other chemical removal assemblies operable to remove one or more coatings from a single-use medical device. The environmental removal assembly can include a temperature controlled removal assembly, a vacuum chamber removal assembly, or other environmental removal assemblies operable to remove one or more coatings from a single-use medical device. The removal assemblies are described in further detail herein.

In another aspect, removing the one or more coatings on the surface of the medical device includes exposing (i.e., contacting) the one or more coatings to denatured ethyl alcohol. The single use medical device can be soaked in denatured ethyl alcohol for about 1 minute to about 5 minutes, about 5 minutes to about 10 minutes, about 10 minutes to about 20 minutes, about 20 minutes to about 30 minutes, about 30 minutes to about 40 minutes, about 40 minutes to about 50 minutes, about 50 minutes to about 60 minutes, or more. In an aspect, the one or more coatings can be wiped from the single-use medical device. A polyester wipe can be sprayed with denatured ethyl alcohol solution (99% denatured ethyl alcohol) and the entire length of the shaft of the single-use medical device containing the one or more coatings can be wiped. The polyester wipe can be sprayed with denatured ethyl alcohol solution 1, 2, 3, 4, 5, 6, 7, 8, 9, 10 or more times to ensure the polyester wipe is completely covered in the denatured ethyl alcohol. The one or more coatings can be wiped 1, 2, 3, 4, 5, 6, 7, 8, 9, 10, 11, 12, 13, 14, 15, 16, 17, 18, 19, 20, or more times until the one or more coatings are completely removed from the surface of the single-use medical device. In an aspect, the one or more coatings are wiped 7 times. The denatured ethyl alcohol can break the bonds of the one or more coatings (e.g., hydrophilic coating) thereby easily removing the one or more coatings from the single-use medical device. In other aspects, the same process can be used to remove the one or more coatings using other solutions such as isopropyl alcohol, a baking soda solution, or other solutions depending on the chemical composition of the one or more coatings.

In some aspects, removing the one or more coatings from the surface of the single-use medical device can include placing the single-use medical device in an ultrasonic tank containing a solution comprising 3% hydrogen peroxide or enzymatic solutions (e.g., proteases, amylases, and lipases). In some aspects, the tank can contain about 1 gallon to about 2 gallons, about 2 gallons to about 3 gallons, about 3 gallons to about 4 gallons, about 4 gallons to about 5 gallons, or more of 3% hydrogen peroxide solution or enzymatic solutions. The ultrasonic tank can be in fluid communication with an ultrasonic sound emitter and a door. One or more single-use medical devices can be placed in the ultrasonic tank and a locking door can enclose the one or more single-use medical devices in the ultrasonic tank. The ultrasonic emitter can provide an ultrasonic frequency of about 20 Hz to about 25 Hz, 25 Hz to about 30 Hz, about 30 Hz to about 35 Hz, about 35 Hz to about 40 Hz, or more to the ultrasonic tank. The ultrasonic tank can act to clean and decontaminate all the components of the single use medical device (e.g., shaft, luer, strain relief, etc.), remove any remaining coating from the single use medical device, and clean an interior lumen of the single-use medical device. In some aspects, the ultrasonic treatment time can be about 1 minute to about 5 minutes, about 5 minutes to about 10 minutes, about 10 minutes to about 15 minutes, about 15 minutes to about 20 minutes, about 20 minutes to about 25 minutes, about 25 minutes to about 30 minutes, 30 minutes to 1 hour, or more. In some aspects, other fluids can be used in the ultrasonic tank such as detergents and other decontamination solutions.

In some aspects, the single-use medical device can be rinsed with water to remove any residual coatings after removal of the coatings. Water (e.g., RO water) can be provided to the single-use medical device via one or more nozzles or spraying manifolds at a flow rate of about 2.5 gallons/minute to about 3.5 gallons/min. In some aspects, the water can have a temperature of about 15 degrees C. to about 30 degrees C.

At block 106, the method 100 can include validating that the one or more coatings have been completely removed from the surface of the single-use medical device. Validation that the one or more coatings have been completely removed from the surface of the single-use medical device can be accomplished by the detection assemblies described herein. Validation of removal of the coatings can ensure that single-use medical device is ready to have a new coating or coatings applied to it. In other aspects, validation can be manually conducted by an operator visually inspecting the surface of the single-use medical device for any trace amounts of coating.

At block 108, the method 100 can include validating that a surface of the integrity of the single-use medical device is sufficient to apply one or more new coatings. Validation of the surface integrity can be an important step in the method 100. The surface integrity of the single-use medical device should be in precise condition (e.g., meeting original manufacturing tolerances) in order to apply a new coating and eventually use in a medical procedure. In an aspect, validation of the surface integrity can use one or more of the detection assemblies described herein. In another aspect, the surface integrity can be tested using methods known in the art that were used prior to applying the original one or more coatings to the medical device.

At block 110, the method 100 can include preparing the surface of the single-use medical device for the one or more new coatings. Preparing the surface of the single-use medical device can include rinsing, cleaning, drying and sterilizing the single-use medical device. By preparing the surface of the single-use medical device prior to applying the one or more new coatings, it can be ensured that the medical device is in condition for use in a patient.

In some aspects, preparing the surface of the single-use medical device can include placing the single-use medical device in an ultrasonic tank containing a solution comprising 3% hydrogen peroxide or enzymatic solutions. In some aspects, the tank can contain about 1 gallon to about 2 gallons, about 2 gallons to about 3 gallons, about 3 gallons to about 4 gallons, about 4 gallons to about 5 gallons, or more of 3% hydrogen peroxide solution or enzymatic solutions. The ultrasonic tank can be in fluid communication with an ultrasonic sound emitter and a door. One or more single-use medical devices can be placed in the ultrasonic tank and a locking door can enclose the one or more single-use medical devices in the ultrasonic tank. The ultrasonic emitter can provide an ultrasonic frequency of about 20 Hz to about 25 Hz, 25 Hz to about 30 Hz, about 30 Hz to about 35 Hz, about 35 Hz to about 40 Hz, or more to the ultrasonic tank. The ultrasonic tank can act to clean and decontaminate all the components of the single use medical device (e.g., shaft, luer, strain relief, etc.), remove any remaining coating from the single use medical device, and clean an interior lumen of the single-use medical device. Decontamination can include removing soils, blood, biological materials, and any other materials on the surface of the single-use medical device. In some aspects, the ultrasonic treatment time can be about 1 minute to about 5 minutes, about 5 minutes to about 10 minutes, about 10 minutes to about 15 minutes, about 15 minutes to about 20 minutes, about 20 minutes to about 25 minutes, about 25 minutes to about 30 minutes, minutes to 1 hour, or more. In some aspects, other fluids can be used in the ultrasonic tank such as detergents and other decontamination solutions.

In an aspect, preparing the surface of the single-use medical device can further include soaking the single-use medical device in 3% hydrogen peroxide solution or enzymatic solutions. The single-use medical device can be placed in an exposure tank containing about 1 gallon to about 2 gallons, about 2 gallons to about 3 gallons, about 3 gallons to about 4 gallons, about 4 gallons to about 5 gallons, or more of 3% hydrogen peroxide solution or enzymatic solutions. The tank can be enclosed by a door. A constant pressure of about 20 psi to about 25 psi, about 25 psi to about 30 psi, about 30 psi to about 35 psi, about 35 psi to about 40 psi, about 40 psi to about 45 psi, about 45 psi to about 50 psi, about 50 psi to about 55 psi, about 55 psi to about 60 psi, or more can provided within the exposure tank. The single-use medical device can be soaked for about 1 minute to about 5 minutes, about 5 minutes to about 10 minutes, about 10 minutes to about 15 minutes, about 15 minutes to about 20 minutes, about 20 minutes to about minutes, about 25 minutes to about 30 minutes, or more. The exposure tank can then be flushed removing all of the fluid from the tank. The soaking procedure can ensure that the single-use medical device is properly cleaned and decontaminated. In some aspects, when an enzymatic solution is used, the tank does not need to be closed or pressurized.

In some aspects, the single-use medical devices can be placed in an enzymatic solution and soaked in the enzymatic solution. In an aspect, the single-use medical devices can be soaked in the enzymatic solution one, two, three, four, or more times. In some aspects, each soak can be about 1 minute to about 3 minutes, about 3 minutes to about 6 minutes, about 6 minutes to about 8 minutes, about 8 minutes to about minutes, or more. In some aspects, a pump can be used to circulate the enzymatic solution in a tank for all of the soaking procedures, one or the soaking procedures, or some of the soaking procedures. In an aspect, the temperature of the enzymatic solution can be about 15 degrees C. to about 30 degrees C. In an aspect, the enzymatic solution can be 1 gallon enzymatic solution and 5 gallons of RO water.

In an aspect, the preparing the surface of the single-use medical device can include wiping the luer and strain relief of the single-use medical device with a polyester wipe that has been sprayed with 3% hydrogen peroxide solution or enzymatic solutions. In some aspects, the luer and the strain relief can be wiped 1, 2, 3, 4, 5, 6, 7, 8, 9, 10, or more times. In an aspect, other detergents can be used such as isopropyl alcohol or other decontaminating agents.

In another aspect, preparing the surface of the single-use medical device can include rinsing the single-use medical device. The single-use medical device can be placed in a rinse tank containing about 1 gallon to about 2 gallons, about 2 gallons to about 3 gallons, about 3 gallons to about 4 gallons, about 4 gallons to about 5 gallons, or more of water.

The rinse tank can be in fluid communication with a pump. The pump can provide a pressure of about 20 psi to about 25 psi, about 25 psi to about 30 psi, about 30 psi to about 35 psi, about 35 psi to about 40 psi, about 40 psi to about 45 psi, about 45 psi to about 50 psi, about 50 psi to about 55 psi, about 55 psi to about 60 psi, or more to the tank. The same pump or another pump can provide a flow rate of water in the rinse tank. The flow rate of water can be about 2 gal/min to about 2.5 gal/min, about 2.5 gal/min to about 3 gal/min, about 3 gal/min to about 3.5 gal/min, about 3.5 gal/min to about 4 gal/min, about 4 gal/min to about 4.5 gal/min, about 4.5 gal/min to about 5 gal/min or more. The temperature of the water can be about 10 degrees C. to about 15 degrees C., about 15 degrees C. to about 20 degrees C., about 20 degrees C. to about 25 degrees C., about 25 degrees C. to about 30 degrees C., or more. In some aspects, the pump can supply the water to an empty tank or the tank can already be filled with water that is provided pressure to move the water. The tank can have a drain that drains the water. In an aspect, the rinse time can be about 1 minute to about 2 minutes, about 2 minutes to about 3 minutes, about 3 minutes to about 4 minutes, about 4 minutes to about 5 minutes, about 5 minutes to about 6 minutes, about 6 minutes to about 7 minutes, about 7 minutes to about 8 minutes, about 8 minutes to about 9 minutes, about 9 minutes to about 10 minutes, or more.

In some aspects, preparing the surface of the single-use medical device can include drying the single-use medical device. In some aspects, the single use medical device can be provided warm air at a temperature of about 20 degrees C. to about 40 degrees C., or about 40 degrees C. to about 150 degrees C., to dry the single-use medical device. In other aspects, industrial dryers can be used. In further aspects, the single-use medical devices can be allowed to sit to dry for a period of time. In some aspects, the period of time can be about 1 minute to about 2 minutes, about 2 minutes to about 3 minutes, about 3 minutes to about 4 minutes, about 4 minutes to about 5 minutes, about 5 minutes to about 6 minutes, about 6 minutes to about 7 minutes, about 7 minutes to about 8 minutes, about 8 minutes to about 9 minutes, about 9 minutes to about 10 minutes, or more.

After preparing the surface of the single-use medical device, the single-use medical device can undergo a final inspection before a new coating is applied. The final inspection can ensure that the prepared surface is sufficient for a new coating to be applied. The final inspection can include using the detection assemblies described herein or visual inspection of the single-use medical device. After the final inspection the single-use medical device can be wiped with a polyester wipe containing 3% hydrogen peroxide solution or enzymatic solutions. The single-use medical device can be wiped 1, 2, 3, 4, 5, 6, 7, 8, 9, 10, or more times. The single-use medical device can also be wiped with a polyester wipe containing 70% isopropyl alcohol solution. The single-use medical device can be wiped 1, 2, 3, 4, 5, 6, 7, 8, 9, 10, or more times. A new coating can then be applied to the single-use medical device.

The method 100 can further include applying the one or more new coatings and validating the one or more new coatings. Validating the new coating can be conducted using the detection assemblies described herein. Further, the one or more new coatings can be tested to validate them. The one or more new coatings can be testing using methods known in the art such as friction tests, hydration tests, length measurements, force tests, or other methods known in the art to ensure that the one or more new coatings have the proper friction parameters for use in a patient.

(I) Detecting a Coating on a Surface of the Single-use Medical Device

The method of this disclosure commences by detecting the one or more coatings on a single-use medical device. The single medical use device may also include a lubricant on the coating. The detection of the one or more coatings can apply to any of the types of coatings and lubricants described herein. In some aspects, the single-use medical device has already been used in a patient and is ready for reprocessing. In other aspects, reprocessing the single-use medical device can occur when the one or more coatings did not pass validation tests and the single-use medical device was never used in a patient. There can be other reasons for reprocessing a single-use medical device, such as the one or more coatings on the single-use medical device have passed an expiration date or other reasons for the single-use medical device being unable to be used in a patient.

Detection assemblies can be used to detect the one or more coatings. The detection assemblies described herein can be used independently or in combination with each other. The first step in detecting the one or more coatings can be determining a number of coatings on the single-use medical device. Then, for each coating the chemical composition (e.g., type) of coating, the thickness of the coating, mass of the coating, the length of the coating, the width of the coating, and the relative geometry of the polymeric coating can be detected. With this knowledge, the appropriate method and parameters of removing the coating can be utilized to ensure the single-use medical device is properly reprocessed. In some aspects, the type of coating can be known prior to the detection of the coating. When the type of coating is known, the detection step can determine the thickness, mass, length, width, and relative geometry of the coating. Determining these parameters can be important for determining the proper removal method and parameters, since the coating can change during use and have different parameters than when it was initially manufactured.

The detection step can utilize detection assemblies such as, but not limited to, a light assembly, a fluid assembly (e.g., liquid or humidity assembly), a magnification assembly, a dye assembly, an AI based detection assembly, a scanning electron microscope assembly, and/or a differential scanning calorimetry assembly.

The detection assemblies can be used for a light detection method, a fluid detection method, a magnification method, a dye method, an artificial intelligence method, a scanning electron microscope method, a differential scanning calorimetry method, or combinations thereof.

The light assembly can include one or more light sources configured to provide a light to the surface of the single-use medical device. In some aspects, the one or more light sources can be LEDs, laser diodes, or other light sources known in the art. In an aspect, the one or more light sources can be configured to provide a light having a wavelength of about 100 nm to about 1200 nm. The one or more light sources can be operable to provide light to the entire surface area of the single-use medical device.

The light assembly can further include one or more sensors to detect reflected and/or refracted light from the single-use medical device. In some aspects, the one or more sensors can be photodetectors. The light received at the sensors can be used to determine the chemical composition, length, width, mass, and geometry of each coating on the single-use medical device. The reflection and/or refraction of light from the one or more coatings on the single-use medical device can be different from the reflection and/or refraction of light from the uncoated sections of the single-use medical device. The reflection and/or refraction data received at the one or more sensors can be used to determine the length, width, mass, and geometry of each coating on the single-use medical device. The reflection and/or refraction data can determine the length of the coating by determining where the change in reflection and/or refraction data begins and ends. By determining where the change in the data begins and ends, the length between the beginning point and the ending point can be measured thereby providing the length of the coating. Similarly, the width of the coating can be determined by determining a beginning point and an ending point in a change in reflection and/or refraction properties of the data received and measuring the distance between the beginning point and the ending point. Similarly, the thickness of the coating can be determined by determining a beginning point and an ending point in a change in reflection and/or refraction properties of the data received and measuring the distance between the beginning point and the ending point. Similarly differences in thickness through the length of the one or more coatings (e.g., non-uniform geometries) can also be detected using reference points (e.g., where reflection/refraction properties differ). The number of coatings can also be determined by the differences in reflection/refraction of light between the coatings and the non-coated sections of the single-use medical device.

The chemical composition of the coating can be determined by determining the reflection/refraction properties of the coating and comparing those reflection/refraction properties to reflection/refraction properties of coatings known in the art. Once the chemical composition is determined, the type of coating is determined based on the chemical composition. The mass of the coating can be determined by determining a density of the type of coating and multiplying the density by the volume of the coating. The volume of the coating can be determined from the determined length, width, and thickness of the coating. In some aspects, the properties of the coating can be determined by a processor in electronic communication with the one or more sensors (e.g., photodetectors).

In another aspect, a fluid assembly can be used to detect the one or more coatings. The fluid assembly can be configured to determine a chemical composition, a mass, a length, a width, and a thickness of each coating on the single-use medical device. The fluid assembly can include a fluid chamber (e.g., liquid chamber or humidity chamber) operable to contain a fluid. The chamber can also be operable to hold the single-use medical device. The fluid chamber can have a door operable to enclose the chamber. In some aspects, the door can be a transparent door. The fluid can be water or another fluid operable to interact and cause chemical interactions to the one or more coatings on the single use medical device. In another aspect, the fluid can be humidified air operable to cause chemical interactions with the one or more coatings. In another aspect, the fluid can be provided by one or more nozzles in fluid communication with the fluid chamber. For hydrophilic coatings, the chemical interaction between the fluid and the coating can cause the coating to expand.

The fluid assembly can further include a machine vision system. The machine vision system can be operable to determine the chemical composition (e.g., type), the mass, the length, the width, and the type of each coating. The machine vision system can determine the chemical composition (e.g., type) of each coating by analyzing the chemical interactions between the fluid and the one or more coatings. Hydrophilic coatings can become lubricous and/or expand when exposed to the fluid. The interactions can provide data to the machine vision system and the machine vision system can determine the chemical composition based on machine learning methods or other methods known in the art. The non-coated portions of the single use medical device can have different chemical interactions than the one or more coatings, thereby providing reference points (e.g., the points where the single-use medical device begins reacting differently) to determine the various parameters of the one or more coatings. The machine vision system can determine the length of the coating by determining a beginning point and an end point of the chemical interactions between the one or more coatings and the fluid as compared to the interactions (or lack thereof) of the non-coated portions of the single-use medical device. Similarly, the machine vision system can determine a thickness and a width of each coating by analyzing a beginning point and an end point between the chemical interactions of the coating with the fluid and measure a distance between the beginning point and the end point (e.g., reference points). Similarly differences in thickness through the length of the one or more coatings (e.g., non-uniform geometries) can also be detected using reference points (e.g., differences in chemical interactions). The mass of the coating can be determined by the density of the determined type of coating and the volume of the measured length, width, and thickness. The number of coatings can also be determined by the differences in chemical interactions between the coatings and the non-coated sections of the single-use medical device.

Alternatively, or in conjunction with the machine vision system, the fluid assembly can include proximity sensors. The proximity sensors can be operable to determine the distances between the reference points (e.g., where chemical interactions of the single-use medical device change), thereby determining the length, width, and thickness of each coating. In other aspects, the single-use medical device can be visually observed by an operator and measured/calculated by hand or other methods known in the art to determine the chemical composition, mass, length, width, thickness, geometry, and number of coatings.

In an aspect, using the fluid assembly, the inherent physical properties of the hydrophilic polymeric coating are used. The hydrophilic polymeric coating expands in the presence of this liquid (polar solvent) to provide the expanded coating. This expanded coated section can easily be differentiated from an uncoated surface section of the single-use medical device.

The dye assembly can include a dye applicator. The dye application can be configured to provide a dye to the single-use medical device. In some aspects, the dye stains the one or more coatings on the single-use medical device but does not stain the uncoated sections of the single-use medical device. In some aspects, the dye assembly can also include a cleaning nozzle operable to provide water to the single-use medical device, thereby removing excess dye from the uncoated portions of the single-use medical device while the one or more coatings remained stained. The dye can be a non-polar dye. These non-polar dyes such as Congo Red are contacted with the single-use medical device and will react with the one or more coatings due to the polarity of the one or more coatings (e.g., hydrophilic coatings). This reaction will stain or color the section comprising the one or more coatings. By staining or coloring the portion of the medical device, the effective length of the coating and the base chemical of the one or more coatings can be determined depending on the non-polar dye utilized. In some aspects, the dye can be Congo Red, Sirius Red F3B, azo dyes, or other dyes known in the art configured to stain a hydrophilic coating.

Similar to the fluid assembly, the dye assembly can include a machine vision system. The machine vision system can be operable to determine the chemical composition of each coating by determining the level of stain of the dye on each coating (e.g., the absorption of the dye on the coating). The absorption characteristics, in conjunction with machine learning, can be used by the machine vision system to determine the chemical composition (e.g., type) of the one or more coatings on the single-use medical device. The machine vision system can determine the length, width, and thickness of the one or more coatings by using reference points (e.g., where the single-use medical device transitions from stained to not stained). Similarly differences in thickness through the length of the one or more coatings (e.g., non-uniform geometries) can also be detected using reference points. The reference points can distinguish between the one or more coatings and the uncoated sections of the single use medical device. The machine vision system can then measure the distances between the reference points to determine the length, width, and thickness. The machine vision system can then calculate the volume of each coating. Using the density of the determined type of coating, the machine vision system can determine the mass of the coating. Similar to the fluid assembly, the dye assembly can utilize proximity sensors to determine the length, width, and thickness of the one or more coatings. Further, an operator can manually determine the parameters of the one or more coatings after the dye is applied by determining distances between stained portions and the absorption of the stained coatings.

Another method for detecting the one or more coatings is magnification. This magnification can be used by a person or a sensor to determine the surface roughness or other visual cues to determine between the coated sections and the uncoated section. This method additionally provides the relative geometry of the polymeric coating.

Artificial Intelligence (AI) can be used to detect the one or more coatings. The AI system can be properly trained to determine the coated versus the non-coated sections from an image or a series of images. The image or images, after analysis by an AI system, will also be able to determine the effective length of the coating. In some aspects, the AI system can determine the length, width, thickness, chemical composition, geometry, and mass of the one or more coatings using images taken of the coating and machine learning methods to train the AI system.

Another detection assembly is a scanning electron microscope assembly. The scanning electron microscope will allow a user to determine a change in the material surface characteristics of the one or more coatings. This instrument will also allow for the identification of the number, length, width, thickness, mass, geometry (e.g., uniform or non-uniform), and chemical composition of the one or more coatings. In some aspects, the scanning electron microscope can be in communication with the AI system to determine the parameters. In another aspect, the machine vision system described above can be used in conjunction with the scanning electron microscope. In another aspect, an operator can determine the characteristics of the coating with the scanning electron microscope.

Another detection assembly is a differential scanning calorimetry (DSC) assembly. The DSC assembly can include a heating element operable to provide heat to the single-use medical device. The heating element can provide heat at a temperature of about 50 degrees C. to about 60 degrees C., about 60 degrees C. to about 70 degrees C., about 70 degrees C. to about 80 degrees C., about 80 degrees C. to about 90 degrees C., about 90 degrees C. to about 100 degrees C., about 110 degrees C. to about 120 degrees C., about 120 degrees C. to about 130 degrees C., about 130 degrees C. to about 140 degrees C., about 140 degrees C. to about 150 degrees C., about 150 degrees C. to about 160 degrees C., about 160 degrees C. to about 170 degrees C., about 170 degrees C. to about 180 degrees C., about 180 degrees C. to about 190 degrees C., about 190 degrees C. to about 200 degrees C., about 200 degrees C. to about 210 degrees C., about 210 degrees C. to about 220 degrees C., about 220 degrees C. to about 230 degrees C., about 230 degrees C. to about 240 degrees C., about 240 degrees C. to about 250 degrees C., about 250 degrees C. to about 260 degrees C., about 260 degrees C. to about 270 degrees C., about 270 degrees C. to about 280 degrees C., about 280 degrees C. to about 290 degrees C., about 290 degrees C. to about 300 degrees C., or more.

The DSC system will clearly show the material composition and may provide the mass or quantity of the hydrophilic polymeric coating and will show this change in the material composition, mass, and/or quantity when the medical device is exposed to heat. The output from the DSC will also show the chemical composition based on the heat flow characteristics of the one or more coatings. The DSC assembly can also be in communication with a machine vision system and/or an AI system as discussed herein. Further, the DSC assembly can be operated by a trained user to determine the parameters of the one or more coatings. The length, width, thickness, and geometry of the one or more coatings can be determined by determining reference points (e.g., points where heat flow information changes between the one or more coatings and the uncoated portions of the single-use medical device) and calculating distances between these reference points. The mass can then be determined by multiplying the density of the one or more coatings (e.g., determined by the type/chemical composition of the coating) by the volume of the coating (e.g., length times width times thickness).

One or more of these detection methods may be used in detection of the one or more coatings.

II. Removing the Coating of the Single-use Medical Device

The next step in the method removes the one or more coatings from the single-use medical device. In order to reprocess the single-use medical device, the one or more coatings need to be removed to ensure the surface can accept the one or more new coatings.

These two steps, the detection and removal of the hydrophilic coating may be complex due to the geometry of the one or more coatings on the single medical-use device or the number of coatings on the single medical-use device. The one or more coatings of the single-use medical device may have a geometry which is uniform or a non-uniform geometry. A "uniform" geometry generally indicates that the surface of the one or more coatings is relatively smooth and consistent. A "non-uniform" geometry relatively indicates that there are relative high points (peaks) and low points (valleys) in the one or more coatings. The removal of the one or more coatings removes the one or more coatings but also maintains the surface and integrity of the single medical-use device.

Removal of the one or more coatings can include utilizing one or more removal assemblies. The removal assemblies can be mechanical removal assemblies, chemical removal assemblies, environmental removal assemblies, and combinations thereof. In some aspects, the mechanical removal assemblies can be one or more of an ultrasonic removal assembly, a water jet removal assembly, a solvent removal assembly, a bead blasting removal assembly, a laser removal assembly, other mechanical removal assemblies, and combinations thereof. The chemical removal assemblies can include an electrostatic charge assembly, an acidic removal assembly, an alkaline removal assembly, other chemical removal assemblies, and combinations thereof. The environmental removal assemblies can include a temperature controlled assembly, a vacuum chamber assembly, other environmental removal assemblies, and combinations thereof. The removal assemblies can be used for mechanical removal methods, chemical removal methods, and environmental removal methods.

The removal assemblies can be used for removal methods. The removal methods can be an ultrasonic removal method, a high-pressure water jet removal method, a bead blasting method, a laser removal method, or a combination thereof. The removal methods can further include providing an electrostatic charge to the one or more coatings, providing an acidic solution to the one or more coatings, providing a basic solution to the one or more coatings, or combinations thereof. The removal method can further include heating the one or more coatings to a temperature above a melting point of the one or more coatings, cooling the one or more coatings to freeze the one or more coatings, or placing the one or more coatings in a vacuum chamber.

Importantly, the geometries determined in the detection step can be used to determine the parameters of the removal step. The length and/or width of the one or more coatings can determine where the removal assemblies are applied (e.g., some of the removal assemblies described herein can be applied only to the one or more coatings and not to the uncoated sections of the single-use medical device). The thickness of the one or more coatings can determine a duration of the removal step. Further, the thickness can determine which removal assembly is used.

The ultrasonic removal assembly can include an ultrasonic tank and an ultrasonic emitter. In some aspects, the ultrasonic tank can include a door configured to enclose the ultrasonic tank. The ultrasonic tank can be configured to contain a liquid and the single-use medical device. The liquid can be water, denatured ethyl alcohol, 3% hydrogen peroxide solution, isopropyl alcohol, a baking soda solution, other detergents, enzymatic solutions, or combinations thereof. The ultrasonic emitter can be configured to emit ultrasonic sound waves into the ultrasonic tank. The ultrasonic sound waves can have a frequency of about 20 Hz to about 40 Hz, or more. The ultrasonic sound waves can create cavitation in the liquid. The cavitation can cause the one or more coatings on the single-use medical device to be removed. In some aspects, the thickness, length, geometry, chemical composition, and mass of the one or more coatings can be used to determine a duration for that the ultrasonic removal assembly provides ultrasonic sound waves. In some aspects, the duration can be about 30 seconds to about 1 minute, about 1 minute to about 5 minutes, about 5 minutes to about 10 minutes, about 10 minutes to about 15 minutes, about 15 minutes to about 20 minutes, about 20 minutes to about 25 minutes, about 25 minutes to about 30 minutes, or more. The ultrasonic chamber can have a temperature of about 50 degrees C. to about 60 degrees C., about 60 degrees C. to about 70 degrees C., about 70 degrees C. to about 80 degrees C., about 80 degrees C. to about 90 degrees C., or more. In an aspect, the temperature can be controlled by a heating and/or cooling element, heat exchangers, or other devices configured to control temperature within a chamber.

The water jet removal assembly can include a tank and one or more high pressure nozzles configured to provide a fluid to the single-use medical device. The one or more high pressure nozzles can spray a cleaning solution on to the one or more coatings. In some aspects, the one or more high pressure nozzles can be configured such that only the one or more coatings are sprayed and the noncoated sections of the single-use medical device are not sprayed. By controlling the areas of the single-use medical device that are sprayed, the surface integrity of the single-use medical device can be maintained. In some aspects, the fluid can be water, denatured ethyl alcohol, 3% hydrogen peroxide solution, 70% isopropyl alcohol, enzymatic solutions, or other detergents. The tank can have a drain to allow excess fluid to flow out of the tank, such that the single-use medical device is not immersed in fluid. In some aspects, the one or more high pressure nozzles provide the fluid at a pressure of about 1,000 psi to about 5,000 psi, about 5,000 psi to about 10,000 psi, about 10,000 psi to about 15,000 psi, about 15,000 psi to about 20,000 psi, or more. In some aspects, the thickness, length, geometry, chemical composition, and mass of the one or more coatings can be used to determine a duration for that the water jet removal assembly provides fluid to the one or more coatings. In some aspects, the duration can be about 30 seconds to about 1 minute, about 1 minute to about 5 minutes, about 5 minutes to about 10 minutes, about 10 minutes to about 15 minutes, about 15 minutes to about 20 minutes, about 20 minutes to about 25 minutes, about 25 minutes to about 30 minutes, or more.

The solvent removal assembly can include a tank containing a solvent. In another aspect, the solvent removal assembly can include a polyester wipe used to wipe the coating off the single-use medical device. The single-use medical device can be placed in the tank containing the solvent for a duration depending on the thickness, length, geometry, chemical composition, and mass of the one or more coatings. The duration can be about 30 seconds to about 1 minute, about 1 minute to about 5 minutes, about 5 minutes to about 10 minutes, about 10 minutes to about 15 minutes, about 15 minutes to about 20 minutes, about 20 minutes to about 25 minutes, about 25 minutes to about 30 minutes, or more. In another aspect, the solvent removal assembly can include a solvent soaked rag or wipe. The solvent soaked rag or wipe can be used to wipe down the one or more coatings thereby removing them. In an aspect, the solvent can be water and alcohols (such as ethanol and iso-propanol). The wiping method can include wiping the one or more coatings 1, 2, 3, 4, 5, 6, 7, 8, 9, 10, 11, 12, 13, 14, 15, 16, 17, 18, 19, or 20 times with a polyester wipe soaked in or sprayed with 99% denatured ethyl alcohol. In one aspect, the one or more coatings can be wiped 7 times to remove the coating. The solvent can be operable to remove the one or more coatings.

The bead blasting removal assembly can include a tank operable to contain the single-use medical device and one or more bead blasting nozzles. The bead blasting nozzles can be configured to blast beads at a high pressure on the one or more coatings. The pressure can be about 1,000 psi to about 5,000 psi, about 5,000 psi to about 10,000 psi, about 10,000 psi to about 15,000 psi, about 15,000 psi to about 20,000 psi, or more. The beads can be crushed or formed dry ice ($CO_2$) or other bead materials configured to remove the one or more coatings. The bead blasting nozzles can be configured to provide beads only to the one or more coatings and not to the noncoated sections of the single-use medical device, thereby preserving the surface integrity of the single-use medical device. The single-use medical device can be placed in the tank containing and blasted with the beads for a duration depending on the thickness, length, geometry, chemical composition, and mass of the one or more coatings. The duration can be about 30 seconds to about 1 minute, about 1 minute to about 5 minutes, about 5 minutes to about 10 minutes, about 10 minutes to about 15 minutes, about 15 minutes to about 20 minutes, about 20 minutes to about 25 minutes, about 25 minutes to about 30 minutes, or more.

The laser removal assembly can include one or more lasers. The one or more lasers can be configured to provide laser beams directly to the one or more coatings thereby removing the one or more coatings from the medical device. The one or more lasers can be configured to only provide laser beams to the coating and not to uncoated portions of the single-use medical device. The lasers can also be configured to provide laser beams to the coatings for a duration that removes the coating but does not damage the underlying surface of the single-use medical device. The wavelength, power, intensity, duration, and frequency of the laser beams can be determined based on the thickness, length, geometry, chemical composition, and mass of the one or more coatings. The wavelength of the laser can be any wavelength between 180 nm to about 2,000 nm. The power of the laser removal system can be about 5 W to about 25 W, or more. The duration can be about 30 seconds to about 1 minute, about 1 minute to about 5 minutes, about 5 minutes to about 10 minutes, about 10 minutes to about 15 minutes, about 15 minutes to about 20 minutes, about 20 minutes to about 25 minutes, about 25 minutes to about 30 minutes, or more.

The electrostatic removal assembly can have a tank operable to contain the single-use medical device and an electrostatic charge emitter (e.g., electrostatic generator). The electrostatic charge emitter can emit an electrostatic charge to the one or more coatings to charge the polarity of the one or more coatings, thereby causing the one or more coatings to be repelled from the surface of the single-use medical device. In some aspects, the electrostatic charge necessary to remove the coating can be determined from the thickness, width, length, chemical composition, and mass of the one or more coatings.

The acidic chemical removal assembly can include a tank operable to contain the single-use medical device and a fluid provider (e.g., nozzle). The fluid provider can provide an acidic chemical to the one or more coatings, thereby causing the coating to dissolve or repel from the surface of the single-use medical device. uses either an acidic or basic chemical. The acidic chemical used and the duration of exposure to the acidic chemical can be determined by the thickness, length, width, chemical composition, and mass of the one or more coatings. The alkaline chemical removal assembly can provide an alkaline chemical in the same manner. The acidic removal assembly and/or alkaline removal assembly can include wiping the one or more coatings with a polyester wipe containing or sprayed with the acidic chemical or base chemical one or more times.

The temperature controlled removal assembly can include a tank configured to contain the single-use medical device. The temperature controlled assembly can have a heating element or a cooling element. The heating element can be configured to provide a temperature of about 100 degrees C. to about 150 degrees C., about 150 degrees C. to about 200 degrees C., about 200 degrees C. to about 250 degrees C., about 250 degrees C. to about 300 degrees C., about 300 degrees C. to about 350 degrees C., about 350 degrees C. to about 400 degrees C., about 400 degrees C. to about 500 degrees C., or more. The heating element can heat the one or more coatings such that the one or more coatings melt and are easily removed from the surface of the single-use medical device using mechanical means or simply melting the entirety of the one or more coatings off. The cooling element can provide a temperature of about 0 degrees C. to about −100 degrees C., about −100 degrees C. to about −200 degrees C., or less. The cooling element can be configured to freeze the one or more coatings such that the one or more coatings are easily removed.

The vacuum chamber removal assembly can include a vacuum chamber. The medical device can be placed into a vacuum chamber at the appropriate temperature and vacuum applied. By applying vacuum, the one or more coatings dehydrate or shrink and are separated from the surface.

In some aspects, the method can include soaking the single-use medical devices in a tank containing an enzymatic solution before removing the one or more coatings. The enzymatic solution can have a temperature of about 15 degrees C. to about 30 degrees C. The enzymatic solution can have 1 gallon of enzymatic solution and 5 gallons of RO water. In some aspects, a pump can be used to circulate the enzymatic solution in the tank. In some aspects, the devices can then be rinsed with RO water provided by a water nozzles at a flow rate of about 2.5 gallons/minute to about 3.5 gallons/per minute. The devices can then be visually inspected for any damage, or the detection assemblies can be used to test the devices for any damage. In some aspects, the lumens of the single-use medical device can be cleared using a lumen clearing guidewire.

III. Validating the Surface of the Single-use Medical Device for the Coating Removal The next step in the method involves the validation of the surface of the single-use medical device to ensure removal of the hydrophilic coating. This validation step examines the surface of the single-use medical device generally using the one or more detection assemblies detailed above and ensures the residual hydrophilic polymeric coating is removed. In various embodiments, the hydrophilic coating on the single medical use device is already known including the thickness, chemical composition, and type of hydrophilic coating. In these cases, the detection method may not be needed. Yet, the removal method, step (b), is needed to ensure the coating is removed. After the removal method is complete, the validation method is then conducted. The validation methods utilize one or more of the detection assemblies and methods described above to ensure the hydrophilic coating is removed. In some aspects, validation can occur after every step in the method and at any time to ensure that the single-use medical device is not damaged.

Methods for detecting the layer are described in more detail in Section (I) above. Methods for removal of the hydrophilic polymeric coating are described in more detail in Section II. In some aspects, validation can also include confirming that the surface integrity of the single-use medical device is in sufficient condition to apply one or more new coatings. In an aspect, validation of the surface integrity can be a friction test, a source roughness test, or other tests used when the single-use medical device was originally manufactured.

After evaluation of the single-use medical device surface to determine whether the hydrophilic polymeric coating has been fully removed, the method can proceed in one of two directions: (a) the residual hydrophilic polymeric coating is still present and not totally removed; or (b) the total removal of the hydrophilic coating. If there are residual traces of the hydrophilic polymeric coating present on the surface of the medical device, the medical device is returned to step (b) of the method to ensure all the hydrophilic polymeric coating is removed. If there is no residual hydrophilic polymeric coating present on the surface of the single-use medical device, the surface of the medical device proceeds to the next step, preparing the surface of the single-use medical device.

(IV) Preparing the Surface of the Single-use Medical Device to form a Prepared Surface on the Single-use Medical Device The next step in the method prepares the surface of the single-use medical device. This step involves cleaning the single-use medical device, rinsing the single-use medical device, and drying the single-use medical device. The single-use medical device may be further disinfected and/or sterilized in preparation for the new hydrophilic coating. These steps can be conducted more than one time, conducted in any order, or conducted more than one time in any order. The single-use medical device can be rinsed, cleaned, rinsed a second time, then sterilized. Alternately, the single-use medical device may be cleaned, rinsed, cleaned a second time, rinsed one or more times, and then sterilized.

Cleaning is the removal of foreign material (such as residual inorganic and/or other organic materials) from the surface of the single-use medical device surface after removal of the hydrophilic coating. The cleaning is normally accomplished using a solvent such as water or a mixture of water and ethanol) with detergents or a solvent and enzymatic product and may use presoaking with the detergent and/or enzymatic solution. Thorough cleaning is required before high-level disinfection and/or sterilization because the inorganic and/or other organic materials that remain on the surfaces of instruments would interfere with the adherence of the new hydrophilic coating or coating(s). Single-use medical devices may be cleaned one or more times including presoaking more than one time with the detergent and/or enzymatic solution and/or rinsing to ensure the residual materials are removed.

Cleaning is normally done manually in use areas without mechanical units (e.g., ultrasonic cleaners or washer-disinfectors) or for fragile or difficult-to-clean single-use medical devices. When a washer-disinfector (mechanical methods) is used, care should be taken in loading single-use medical devices. This cleaning step may occur one time, two times, three times, or more than three times.

In some aspects, preparing the surface of the single-use medical device can include placing the single-use medical device in an ultrasonic tank containing a solution comprising 3% hydrogen peroxide. In some aspects, the tank can contain about 1 gallon to about 2 gallons, about 2 gallons to about 3 gallons, about 3 gallons to about 4 gallons, about 4 gallons to about 5 gallons, or more of 3% hydrogen peroxide solution. The ultrasonic tank can be in fluid communication with an ultrasonic sound emitter and a door. One or more single-use medical devices can be placed in the ultrasonic tank and a locking door can enclose the one or more single-use medical devices in the ultrasonic tank. The ultrasonic emitter can provide an ultrasonic frequency of about 20 Hz to about Hz, 25 Hz to about 30 Hz, about 30 Hz to about 35 Hz, about 35 Hz to about 40 Hz, or more to the ultrasonic tank. The ultrasonic tank can act to clean and decontaminate all the components of the single use medical device (e.g., shaft, luer, strain relief, etc.), remove any remaining coating from the single use medical device, and clean an interior lumen of the single-use medical device. In some aspects, the ultrasonic treatment time can be about 1 minute to about 5 minutes, about 5 minutes to about 10 minutes, about minutes to about 15 minutes, about 15 minutes to about 20 minutes, about 20 minutes to about 25 minutes, about 25 minutes to about 30 minutes, or more. In some aspects, other fluids can be used in the ultrasonic tank such as detergents and other decontamination materials.

In an aspect, preparing the surface of the single-use medical device can further include soaking the single-use medical device in 3% hydrogen peroxide solution. The single-use medical device can be placed in a tank containing about 1 gallon to about 2 gallons, about 2 gallons to about 3 gallons, about 3 gallons to about 4 gallons, about 4 gallons to about 5 gallons, or more of 3% hydrogen peroxide solution. The tank can be enclosed by a door. A constant pressure of about 20 psi to about 25 psi, about 25 psi to about 30 psi, about 30 psi to about 35 psi, about 35 psi to about 40 psi, about 40 psi to about 45 psi, about 45 psi to about 50 psi, about 50 psi to about 55 psi, about 55 psi to about 60 psi, or more can provided within the tank. The single-use medical device can be soaked for about 1 minute to about 5 minutes, about 5 minutes to about 10 minutes, about 10 minutes to about 15 minutes, about 15 minutes to about 20 minutes, about 20 minutes to about 25 minutes, about 25 minutes to about 30 minutes, or more. The tank can then be flushed removing all of the fluid from the tank. The soaking procedure can ensure that the single-use medical device is properly cleaned and decontaminated.

In some aspects, the single-use medical devices can be placed in an enzymatic solution and soaked in the enzymatic solution. In an aspect, the single-use medical devices can be soaked in the enzymatic solution one, two, three, four, or more times. In some aspects, each soak can be about 1 minute to about 3 minutes, about 3 minutes to about 6 minutes, about 6 minutes to about 8 minutes, about 8 minutes to about minutes, or more. In some aspects, a pump can be used to circulate the enzymatic solution in a tank for all of the soaking procedures, one or the soaking procedures, or some of the soaking procedures. In an aspect, the temperature of the enzymatic solution can be about 15 degrees C. to about 30 degrees C. In an aspect, the enzymatic solution can be 1 gallon enzymatic solution and 5 gallons of RO water.

In an aspect, the preparing the surface of the single-use medical device can include wiping the luer and strain relief of the single-use medical device with a polyester wipe that has been sprayed with 3% hydrogen peroxide solution. In some aspects, the luer and the strain relief can be wiped 1, 2, 3, 4, 5, 6, 7, 8, 9, 10, or more times. In an aspect, other detergents can be used such as isopropyl alcohol or other decontaminating agents.

In some aspects, the lumen of the single-use medical device can be cleared using a lumen clearing guidewire to remove any excess materials or buildup in the lumen.

After cleaning, the single-use medical device is rinsed. This rinsing step may occur one time, two times, three times, or more than three times and uses one or more polar solvents (such as water or a mixture of water and ethanol). This step ensures the cleaning agent (such as detergents and/or enzymatic products) is adequately removed. The rinsing step may use a polar solvent and/or a mixture of polar solvents (such as water and ethanol).

In another aspect, preparing the surface of the single-use medical device can include rinsing the single-use medical device. The single-use medical device can be placed in a rinse tank containing about 1 gallon to about 2 gallons, about 2 gallons to about 3 gallons, about 3 gallons to about 4 gallons, about 4 gallons to about 5 gallons, or more of water.

The rinse tank can be in fluid communication with a pump. The pump can provide a pressure of about 20 psi to about 25 psi, about 25 psi to about 30 psi, about 30 psi to about 35 psi, about 35 psi to about 40 psi, about 40 psi to about 45 psi, about 45 psi to about 50 psi, about 50 psi to about 55 psi, about 55 psi to about 60 psi, or more to the tank. The same pump or another pump can provide a flow rate of water in the rinse tank. The flow rate of water can be about 2 gal/min to about 2.5 gal/min, about 2.5 gal/min to about 3 gal/min, about 3 gal/min to about 3.5 gal/min, about 3.5 gal/min to about 4 gal/min, about 4 gal/min to about 4.5 gal/min, about 4.5 gal/min to about 5 gal/min or more. The temperature of the water can be about 10 degrees C. to about 15 degrees C., about 15 degrees C. to about 20 degrees C., about 20 degrees C. to about 25 degrees C., about 25 degrees C. to about 30 degrees C., or more. In some aspects, the pump can supply the water to an empty tank or the tank can already be filled with water that is provided pressure to move the water. The tank can have a drain that drains the water. In an aspect, the rinse time can be about 1 minute to about 2 minutes, about 2 minutes to about 3 minutes, about 3 minutes to about 4 minutes, about 4 minutes to about 5 minutes, about 5 minutes to about 6 minutes, about 6 minutes to about 7 minutes, about 7 minutes to about 8 minutes, about 8 minutes to about 9 minutes, about 9 minutes to about 10 minutes, or more. The rinsing step can be conducted between any of the steps described herein.

After the rinsing step, the single-use medical device is dried. This step ensures that the residual rinsing solvent is removed, and the surface of the single-use medical device is prepped to receive the new hydrophilic coating. The drying step may use and elevated temperature, an inert gas, vacuum, compressed air and/or inert gas being blown on the surface and blown through the single-use medical device, or a combination thereof.

In some aspects, the single-use medical device can be flow tested to ensure a proper flow rate through the lumen of the single-use medical device. In an aspect, the flow rate testing can be conducted using ambient water and a pump. In an aspect, after flow testing the inner lumen can be cleaned using pressurized air.

The temperature of the drying step can and will vary depending on the rinsing solvent used. Generally, the temperature of the drying step may range from about 50 degrees C. to about 150 degrees C. In various embodiments, the temperature of the drying step may range from about 50 degrees C. to about 150 degrees C., from about 50 degrees C. to about 75 degrees C., from about 75 degrees C. to about 100 degrees C., from about 100 degrees C. to about 125 degrees C., or from about 125 degrees C. to about 150 degrees C. This drying step may utilize an inert atmosphere such as helium, nitrogen, argon, or a combination thereof and reduced pressure.

In some aspects, the single use medical device can be provided warm air at a temperature of about 20 degrees C. to about 40 degrees C., or about 40 degrees C. to about 150 degrees C., to dry the single-use medical device. In other aspects, industrial dryers can be used. In further aspects, the single-use medical devices can be allowed to sit to dry for a period of time. In some aspects, the period of time can be about 1 minute to about 2 minutes, about 2 minutes to about 3 minutes, about 3 minutes to about 4 minutes, about 4 minutes to about 5 minutes, about 5 minutes to about 6 minutes, about 6 minutes to about 7 minutes, about 7 minutes to about 8 minutes, about 8 minutes to about 9 minutes, about 9 minutes to about 10 minutes, or more. In another aspect, the single-use medical devices can be dried in a vacuum oven.

After preparing the surface of the single-use medical device, the single-use medical device can undergo a final inspection (i.e., validation) before a new coating is applied. The final inspection can ensure that the prepared surface is sufficient for a new coating to be applied. The final inspection can include using the detection assemblies described herein or visual inspection of the single-use medical device. After the final inspection the single-use medical device can be wiped with a polyester wipe containing 3% hydrogen peroxide solution. The single-use medical device can be wiped 1, 2, 3, 4, 5, 6, 7, 8, 9, 10, or more times. The single-use medical device can also be wiped with a polyester wipe containing 70% isopropyl alcohol solution. The single-use medical device can be wiped 1, 2, 3, 4, 5, 6, 7, 8, 9, 10, or more times. A new coating can then be applied to the single-use medical device.

In some aspects, the final inspection can include flow testing, visual inspection using a magnifying lamp, visual inspection using an operator's eyesight, or visual inspection using a microscope. In some examples, for electric single-use medical devices, the final inspection can include capacitance testing by supplying electricity to a power connector of the single-use medical device.

After the drying and final inspection is complete, the surface of the single-use medical device is disinfected and/or sterilized. After disinfection and/or sterilization, the surface preparation step needs to be validated. This validation step ensures traces of the cleaning agent, the rinsing agent, and traces of inorganic and/or or organic materials are removed, and the surface of the single-use medical device is prepared to receive the new hydrophilic coating. The validation can step can use various sensors (e.g., machine mission systems), visual inspection, or other methods to ensure that the single-use medical device has been properly cleaned and dried.

(V) Applying a New Coating on the Prepared Surface of the Single-use Medical Device The next step in the method encompasses applying a new coating on the prepared surface of the single-use medical device. More than one application of the hydrophilic coating may reduce peaks or valleys in the hydrophilic coating. The new hydrophilic coating is generally applied by various methods such as a dip method, a spray method, a painting method, or other methods known in the art according to industrial standards or various custom application methods. In these cases, a solution of the monomer of the hydrophilic polymeric coating and a solvent is prepared and this monomer solution is applied on the prepared surface of the single-use medical device. After the monomer solution is applied, the solvent is evaporated under reduced pressure, vacuum, or a combination thereof and the monomer is cured using UV light. After the curing of the monomer is complete, a hydrophilic polymeric coating is on the surface of the single-use medical device. The coating of the hydrophilic coating can be applied two times, three times, or more than three times to ensure the proper thickness, length, mass, and geometry of the hydrophilic polymeric coating is achieved according to industrial standards.

(VI) Validation of the New Hydrophilic Polymeric Coating on the Single-use Medical Device.

The last step in the method, is a validation that the new hydrophilic polymeric coating on the prepared surface meets the requirements of the single-use medical device. This validation step tests the single medical-use device to ensure the mechanical characteristics of the coating to meet industrial standards. Mechanical properties may be the proper coating or coatings, the thickness of the coating, the length of the coating, the geometry of the coating, or the coating integrity on the single-use medical device. The validation method may also include simulated use and comparison to other similar single-use medical device coatings. If the single-use medical device does not pass this validation step, the single-use medical device would be returned to the previous step to ensure the coating is properly applied. Once the single-use medical device has been validated; the reprocessing step of the single-use medical device is complete.

In some aspects, validation of the new hydrophilic coating can include coating length testing, friction testing, hydrated coating thickness testing, grand average force testing, and other testing methods typically used in the art to ensure the reprocessed single-use medical device is in proper condition for medical use.

Examples

Reprocessing of a single-use medical device having a hydrophilic coating was conducted. The hydrophilic coating comprised a poly(vinylpyrrolidone) (PVP) coating. The coating was first detected using visual inspection and various sensors for determining the length, width, thickness, and geometry of the coating on three lots of single-use medical catheters with PVP coatings. The first lot contained 31 coated single-use medical devices. The second lot contained 30 single-use medical devices. The third lot contained 16 single-use medical devices.

Each single-use medical device was then subjected to enzymatic cleaning in a tank containing an enzymatic solution. The single-use medical devices were soaked in the enzymatic solution (i.e., 1 gallon Metrex MetriZyme Dual Enzymatic Cleaner and 5 gallons RO water) at a temperature range of about 15 degrees C. to about 30 degrees C., or about 65 degrees F. to about 80 degrees F. Each single-use medical device was then submerged by pressing a tray down on the single-use medical device in the enzymatic solution. Each single-use medical device was then rinsed off with reverse osmosis (RO) water at 2.5 gallons/min to about 3.5 gallons per minute provided by a rinse manifold (e.g., pressurized water nozzle) at a temperature of about 15 degrees C. to about 30 degrees C. in a rinse tank. A circulating pump was used to pump the enzymatic solution through the device lumen and clean the inner surfaces.

The single-use medical devices were then visually inspected for any damage to a transition block, tip, guidewire port, or electrical connector of the single-use medical device. The lumen of each single-use medical device was then cleared using a clearing guidewire.

A polyester wipe was sprayed with denatured ethyl alcohol five times. A different polyester wipe was used for each single-use medical device. The entire length of the shaft of each single-use medical device was then manually wiped with each polyester wipe containing the sprayed on denatured ethyl alcohol seven times. The denatured ethyl alcohol broke down the hydrophilic coating and removed the hydrophilic coating from the surface of the single-use medical devices.

Each single-use medical device was then rinsed by providing at 2.5 gallons per minute to 3.5 gallons per minute with the rinse manifold with RO water at a temperature of about 15 degrees C. to about 30 degrees C., or about 65 degrees F. to about 80 degrees F.

Each single-use medical device was then subjected to a second enzymatic soak of 1 gallon of RO water with enzymatic cleaner at a temperature of about 15 degrees C. to about 30 degrees C. or about 65 degrees F. to about 80 degrees F. Each single-use medical device was then submerged in the enzymatic solution using the tray. A circulating pump was used to circulate the enzymatic solution through the device lumen and clean the inner surfaces. The enzymatic soak was repeated for a second time.

A brush was then used to brush the exterior of the single-use medical device. The single-use medical device was then wiped using a polyester wipe. Each single-use medical device was then placed in a sink containing 5 gallons of RO water. The devices were then sprayed with the spraying manifold with RO water at about 2.5 gallons/minute to about 3.5 gallons per/minute at a temperature of about 15 degrees C. to about 30 degrees C.

Some of the single-use medical devices then were flow tested by placing the single-use medical devices in a sink containing ambient water and a pump was run. The pump circulated water through the single-use medical device lumens and flow rates of 690 mL/min to 750 mL/min were confirmed.

At a next step, the surface integrity validation of each single-use medical device was then conducted. Each single-use medical device was tested for line clearance and curvature to ensure that the lines were cleared, and each single-use medical device had a curvature within a minimum tolerance.

Each single-use medical device was then vacuum dried in a vacuum oven for 120 minutes. Each single use medical device was then visually inspected to ensure the surface integrity of the single-use medical device was sufficient for recoating. Each single-use medical device was then cleaned again a polyester wipe for each single-use medical device with 70% isopropyl alcohol and wiped down 5 times. Each single-use medical device was then visually inspected again to ensure none of the single-use medical devices were damaged.

Each single-use medical device was then coated in a new hydrophilic coating. After coating, each recoated single-use medical device was tested for various parameters to ensure the recoated single-use medical devices were within manufacturing tolerances and therefore ready to be used in a patient.

Each single-use medical device in each lot was coated with a PVP hydrophilic coating using ethanol or isopropyl alcohol as a solvent. Each single-use medical device was given a primer coating. Table 1 shows the nominal primer process parameters. Table 2 shows the coating parameters of a hydrophilic coating.

TABLE 1

| Nominal Primer Process Parameters | |
| --- | --- |
| 1x Primer Coat Primer Solution | |
| Parameter Description | Value |
| Dip Length (cm): | 21.2 |
| Cure Time (seconds) | 60 |

TABLE 2

| Nominal Hydrophilic Coating Parameters | |
| --- | --- |
| Ix Hydrophilic Coat Hydrophilic Coating Solution | |
| Parameter Description | Value |
| Dip Length (cm): | 21.0 |
| Cure Energies (mJ)/Cure Times (s) | 300* (390 mJ-1200 mJ) |
| Total Dissolved Solids (TDS %) | 3.80%-5.00% |

10 samples were tested per lot. All testing units met the targeted specifications. All testing units met the targeted specifications. The production resulted in a process capability Ppk=2.12 which is greater than the ideal value of 1.55. The process capability of coating length was Ppk=1.23 which is slightly below the ideal Ppk of 1.55. Process improvements can be made for the coating length quality with improvements to the tube refill quantity and operator training on alignment of the fixtures. The current specification of ±2 cm can be maintained. Frictional force produced a robust process capability of Ppk=26.38. All test samples passed the specification requirements with acceptable capability. This experiment demonstrates within 95%/90% confidence/reliability bounds that the normal variables produce and meets the established acceptance criteria.

For evaluation, the functional/variable data are coating length, lubricity, and hydrated coating thickness; all other parameters that are reported at attribute data, which include coating clarity, coating color, coating inclusions, coating coverage, and tactile coating roughness.

Sample size calculated using the below equation to satisfy a 95%/90% confidence and reliability bound. Using the equation, 29 samples are required to meet the 95%/90% confidence and reliability bounds however 10 will be tested to accommodate for an even representation of all three lots. A summary of the yield and scrap of each PQ lot is listed in Table 3.

$$n =ln(1-CI)/ln(R) \qquad (Eq.\ 1)$$

n is the number of samples required, CI is confidence interval, and R is reliability. Confidence interval and reliability are presented as decimals in Equation 1.

TABLE 3

| | | | Yield/Scrap | | |
| --- | --- | --- | --- | --- | --- |
| Lot # | Certified Qty | Number of Test Articles | Number of Devices Coated | Number of Devices Scrapped | Cause for Scrap |
| 1 | 31 | 10 | 20 | 1 | Coating length on setup unit just outside of specification. |
| 1 | 30 | 10 | 30 | 3 | Distal tip damage (2), Excessive over area (1) |
| 1 | 16 | 10 | 16 | 1 | Part kinked or crushed during coating process |

The coatings to each single-use medical device were applied and then cured using UV light. All UV light measurement data was gathered using an ILT1400A Radiometer system. Machine cassette Positions 7 & 12 were used when measuring light intensities. Validated UV Cure Intensity Range is 1.30 to 4.00 mW/cm2. The UV Cure Intensity reading for each individual bulb used is 1.40 to 4.00 mW/cm2. Table 4 illustrates light intensity data.

TABLE 4

| | UV Intensity Records | | | | | |
| --- | --- | --- | --- | --- | --- | --- |
| | Lot #1 | | Lot #2 | | Lot #3 | |
| UV Light Position | Start of Lot #1 UV intensity (mW/cm$^2$) | End of Lot #1 UV Intensity (mW/cm$^2$) | Start of Lot #2 UV Intensity (mW/cm$^2$) | End of Lot #2 UV Intensity (mW/cm$^2$) | Start of Lot #3 UV Intensity (mW/cm$^2$) | End of Lot #3 UV Intensity (mW/cm$^2$) |
| Position 1 | 1.95 | 2.01 | 2.03 | 1.89 | 1.89 | 1.93 |
| Position 3 | 1.91 | 2.56 | 2.60 | 2.50 | 2.15 | 2.20 |
| Position 2 | 2.55 | 1.94 | 2.34 | 2.30 | 2.02 | 2.07 |
| Position 4 | 2.52 | 2.30 | 1.94 | 1.91 | 2.00 | 2.04 |
| Average | 2.233 | 2.203 | 2.228 | 2.150 | 2.015 | 2.060 |
| Std. Dev. | 0.350 | 0.285 | 0.302 | 0.300 | 0.107 | 0.111 |

For this qualification, the nominal cure time of 300 seconds is used for all three lots. See Equation 2 below for the formula.

$$P = I * t \quad \text{(Eq. 2)}$$

Where P is UV power dosage (mJ), I is UV light intensity measurement (mW/cm²) and t is time.

A moisture analyzer (i.e., HB43-S-Mettler-Toledo Moisture Analyzer) system was used to determine a TDS % (total dissolved solids percentage) during coating during coating. TDS % defined operating range was 3.80% to 5.00%. Table 5 illustrates TDS % at the start of coating and the end of coating for each lot.

TABLE 5

Hydrophilic Coat TDS% Records

| Lot Number | Actual TDS % at start | Actual TDS % at end |
|---|---|---|
| 1 | 3.88 | 4.38 |
| 2 | 4.03 | 4.59 |
| 2 | 3.88 | 4.03 |

The operating conditions for coating were a relative humidity range of less than or equal to 60% and a temperature range of 15.6 degrees C. to 26.7 degrees C. The devices must be coated within these temperature and relative humidity ranges to avoid a risk of absorption of moisture and activating the coating. Data was gatherer using a data logger (e.g., Dickson-One data logger). Table 6 illustrates temperature and humidity for each lot at the start of coating and end of coating.

TABLE 6

Temperature and Humidity Records

| | Lot #1 | | Lot #2 | | Lot #3 | |
|---|---|---|---|---|---|---|
| | Start of Lot #1 | End of Lot #1 | Start of Lot #2 | End of Lot #2 | Start of Lot #3 | End of Lot #3 |
| Temperature in ° F: | 71.9 | 71.8 | 69.3 | 70.2 | 69.6 | 69.4 |
| Relative Humidity in | 25.2 | 25.7 | 23.8 | 28.8 | 33.9 | 32.9 |

Table 7 illustrates surface morphology data gathered using surface morphology testing and Congo Red dye coverage testing. At least 29 samples (n=30) with zero failures achieved 95%/90% confidence/reliability for attribute data.

TABLE 7

Surface Morphology and Coating Length/Thickness Data

| HMS Lot Number | Test Article Number | Tactile Roughness 23 | Coating Color (Transparent) | Coating Clarity (Clear) | Coating Inclusion S0.4 mm² | Coating Voids: Voids adding up to 51.0 mma on TAPPI chart. | Coating Length (cm) | Hydrated Coating Thickness (μ) |
|---|---|---|---|---|---|---|---|---|
| Lot #1 | 1 | 5 | Transparent | Clear | 0.0 | 0.0 | 21.2 | 13.5 |
| | 2 | 5 | Transparent | Clear | 0.0 | 0.0 | 21.3 | 15.5 |
| | 3 | 5 | Transparent | Clear | 0.0 | 0.0 | 21.6 | 20 |
| | 4 | 5 | Transparent | Clear | 0.0 | 0.0 | 22 | 10 |
| | 5 | 5 | Transparent | Clear | 0.0 | 0.0 | 22 | 13.5 |
| | 6 | 5 | Transparent | Clear | 0.0 | 0.0 | 21.9 | 13.5 |
| | 7 | 5 | Transparent | Clear | 0.0 | 0.0 | 21.2 | 7 |
| | 8 | 5 | Transparent | Clear | 0.0 | 0.0 | 22.4 | 3 |
| | 9 | 5 | Transparent | Clear | 0.0 | 0.0 | 21 | 5 |
| | 10 | 5 | Transparent | Clear | 0.0 | 0.0 | 22 | 12 |
| Lot #2 | 1 | 4 | Transparent | Clear | 0.0 | 0.0 | 21 | 15 |
| | 2 | 5 | Transparent | Clear | 0.0 | 0.0 | 21.7 | 13 |
| | 3 | 5 | Transparent | Clear | 0.0 | 0.0 | 22.2 | 16 |
| | 4 | 5 | Transparent | Clear | 0.0 | 0.0 | 21.5 | 15 |
| | 5 | 4 | Transparent | Clear | 0.0 | 0.0 | 21.4 | 14.5 |
| | 6 | 4 | Transparent | Clear | 0.0 | 0.0 | 21.7 | 15 |
| | 7 | 5 | Transparent | Clear | 0.0 | 0.0 | 21.3 | 14.5 |
| | 8 | 5 | Transparent | Clear | 0.0 | 0.0 | 21.7 | 16 |
| | 9 | 4 | Transparent | Clear | 0.0 | 0.0 | 21.5 | 18.5 |
| | 10 | 5 | Transparent | Clear | 0.0 | 0.0 | 21.3 | 13.5 |
| Lot #3 | 1 | 5 | Transparent | Clear | 0.0 | 0.0 | 21 | 16 |
| | 2 | 5 | Transparent | Clear | 0.0 | 0.0 | 21.2 | 21.5 |
| | 3 | 5 | Transparent | Clear | 0.0 | 0.0 | 21.2 | 23.5 |
| | 4 | 5 | Transparent | Clear | 0.0 | 0.0 | 21.3 | 20 |
| | 5 | 5 | Transparent | Clear | 0.0 | 0.0 | 20.8 | 21.5 |
| | 6 | 5 | Transparent | Clear | 0.0 | 0.0 | 21.1 | 23 |
| | 7 | 5 | Transparent | Clear | 0.0 | 0.0 | 21.8 | 26.5 |
| | 8 | 5 | Transparent | Clear | 0.0 | 0.0 | 21.8 | 20.5 |
| | 9 | 5 | Transparent | Clear | 0.0 | 0.0 | 21 | 20 |
| | 10 | 5 | Transparent | Clear | 0.0 | 0.0 | 21.8 | 20.5 |

The coating length acceptance criteria was 21.0 cm+/−2 cm. Table 7 illustrates coating length for 29 passing samples (n=30). The coating length $Pp_k$ was 1.23 which is slightly below the ideal $Pp_k$ of 1.55. Process improvements can be made for the coating length quality with improvements to tube refill frequency and operator training on alignment of fixtures. At least 29 passing samples (total n=30) with zero failures achieves 95%/90% confidence/reliability for attribute data. Table 8 shows length summary statistics.

TABLE 8

Coating Length Summary Statistics

| Description | Value |
| --- | --- |
| Minimum, Maximum Value | 20.8, 22.4 |
| Mean | 21.50 |
| Standard Deviation | 0.406 |

Figure 2:
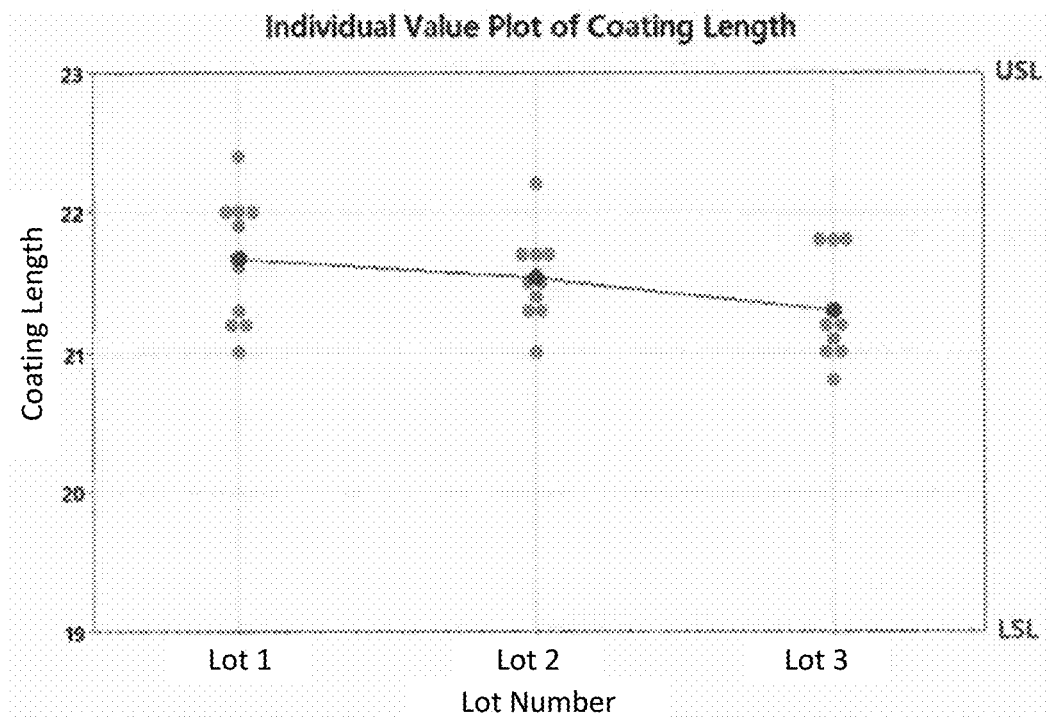
FIG. 2 is an individual value plot of coating length validation.

FIG. 2 illustrates an individual value plot of coating length (cm) for each lot number. The coating length plot has a lower limit of 19 cm and an upper limit of 23 cm.

Figure 3:
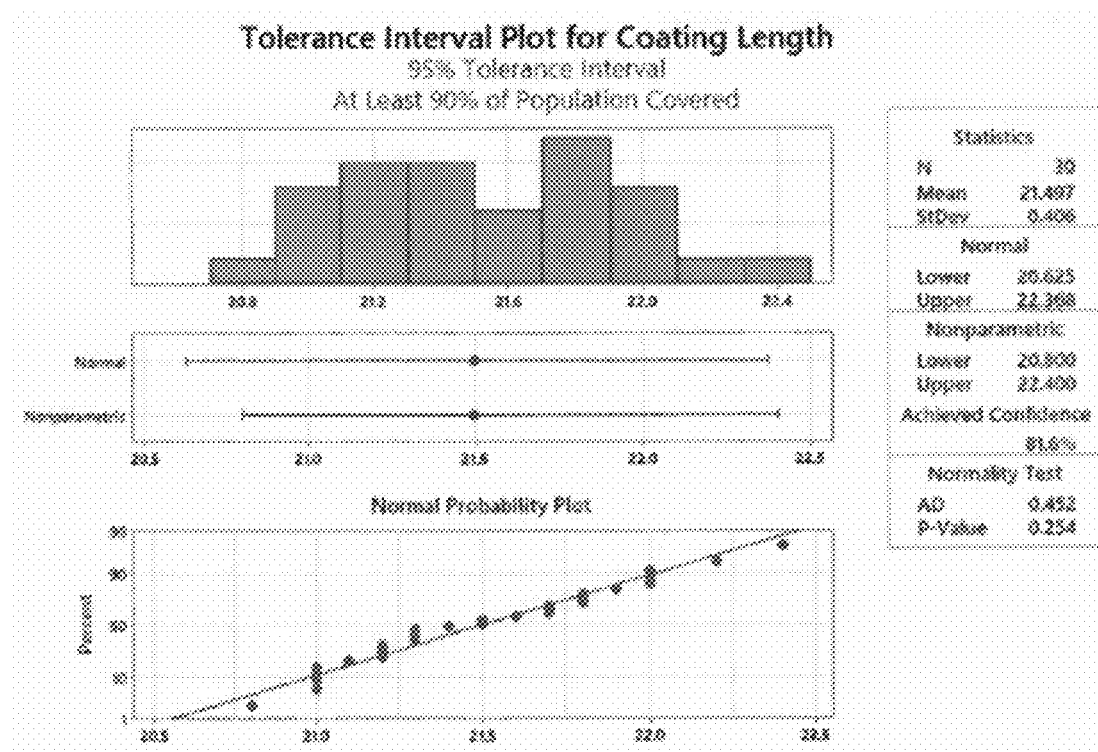
FIG. 3 is a tolerance interval plot for coating length validation.

FIG. 3 illustrates a tolerance interval plot for coating length. Out of 30 samples the mean coating length was 21.497 with a standard deviation of 0.406. An achieved confidence was 81.6%. The normality test had an Ad (Anderson Darling Test) value of 0.452 and a P-value of 0.254.

Figure 4:
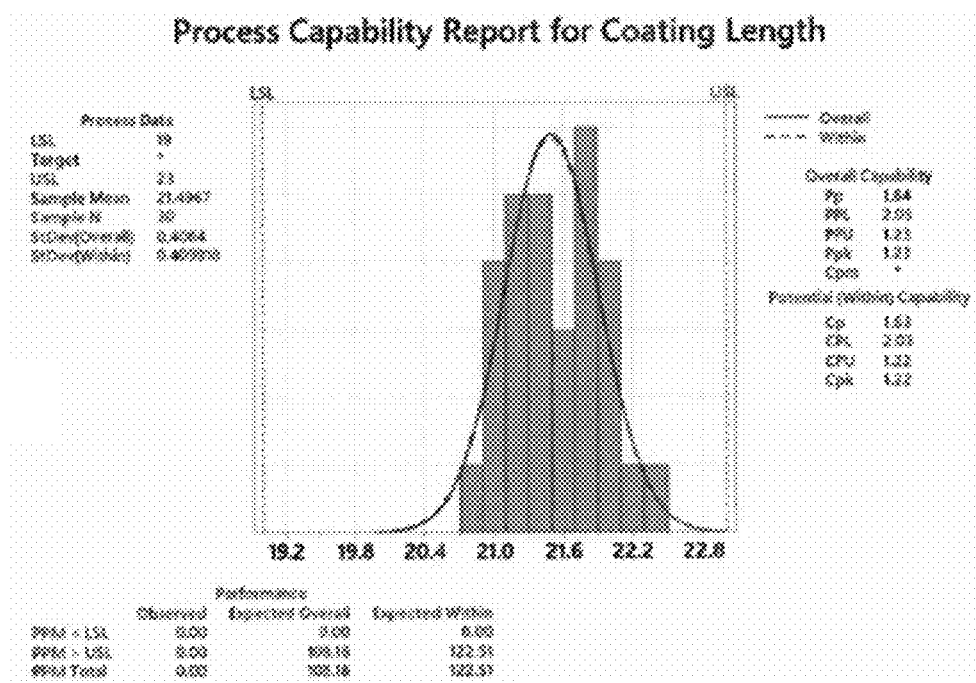
FIG. 4 is a process capability report for coating length validation.

FIG. 4 illustrates the process capability of coating length (cm) showing process data, overall capability, potential capability, and performance.

Next the hydrated coating thickness (μm) was validated. The target criteria was a thickness of less than or equal to 50 μm. The coating thicknesses were gathered using a micrometer measuring instrument (CTS1100 Micrometer Measuring Instrument). All testing units met the targeted specifications. The process capability $Pp_k$ was 2.12 which is greater than the ideal value of 1.55, meaning all the reprocessed single-use medical devices met required thickness specifications. The hydrated diameter was calculated using Equation 3 below.

$$A=(C-B)/2 \quad \text{(Eq. 3)}.$$

Where A is hydrated thickness, B is unhydrated diameter, and C is hydrated diameter. The hydrated coating thickness summary statistics are presented in Table 9. Hydrated thicknesses for each reprocessed single-use medical device is shown in Table 7.

TABLE 9

Hydrated Coating Thickness Summary Statistics

| Description | Value |
| --- | --- |
| Minimum, Maximum Value | 3.00, 13.5 |
| Mean | 15.9 |
| Standard Deviation | 5.37 |

Figure 5:
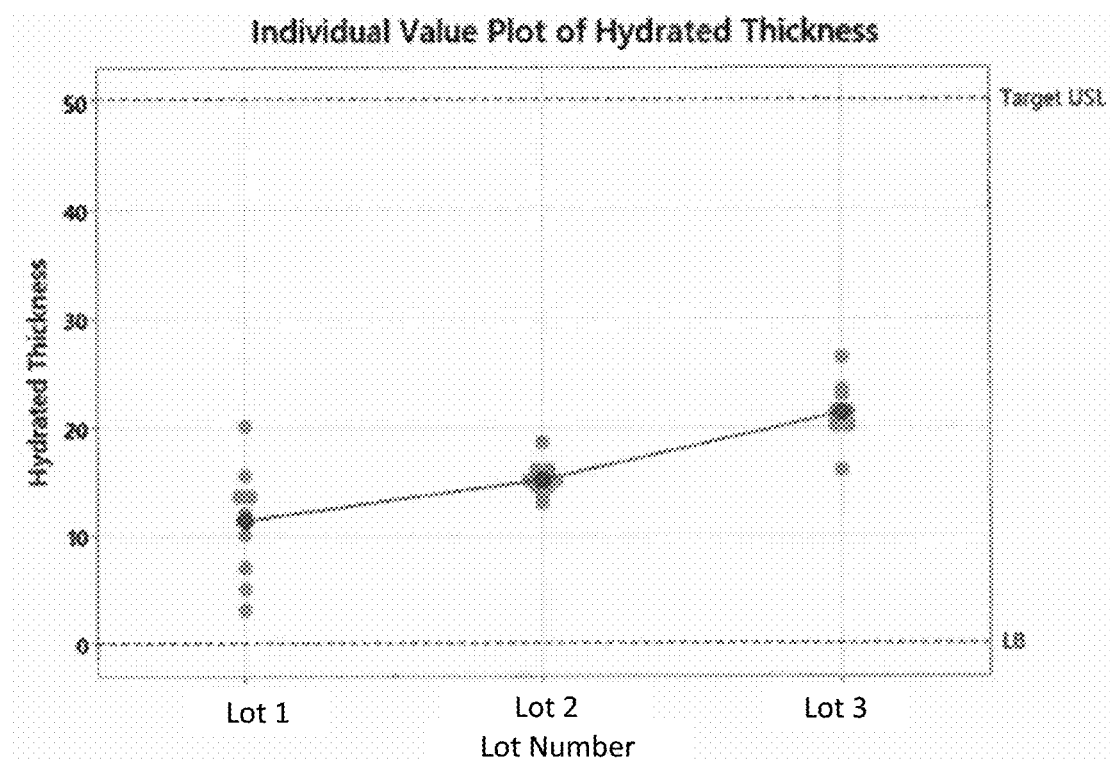
FIG. 5 is an individual value plot of hydrated thickness for reprocessed single-use medical device validation.

FIG. 5 illustrates an individual value plot of hydrated thicknesses for each reprocessed single-use medical device showing lower bounds and upper bounds. As illustrated all of the of the reprocessed single-use medical devices had a coating hydrated thickness within the target of less than or equal to 50 μm.

Figure 6:
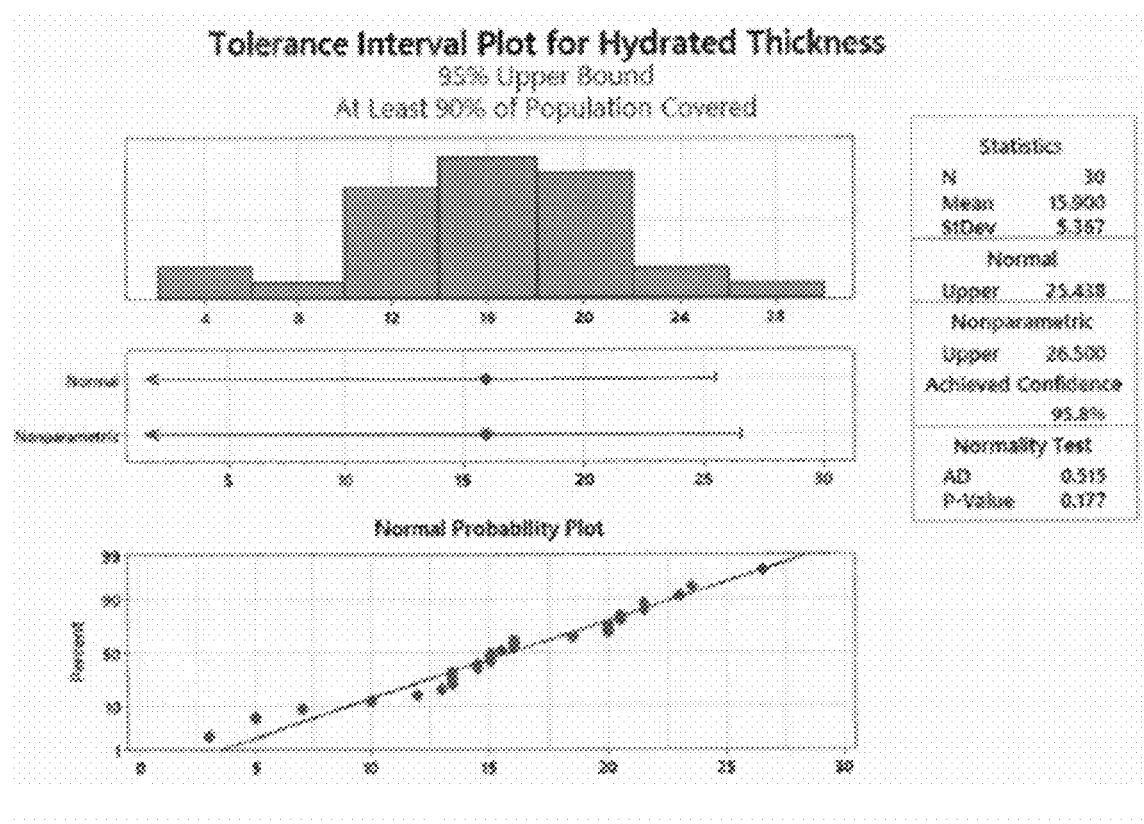
FIG. 6 is a tolerance interval plot for hydrated thickness for reprocessed single-use medical device validation.

FIG. 6 illustrates a tolerance interval plot for hydrated thickness for 30 samples. The mean was 15.900 μm with a standard deviation of 5.367. The achieved confidence was 95.8%. The normality test had an AD value of 0.515 and a p-value of 0.177.

Figure 7:
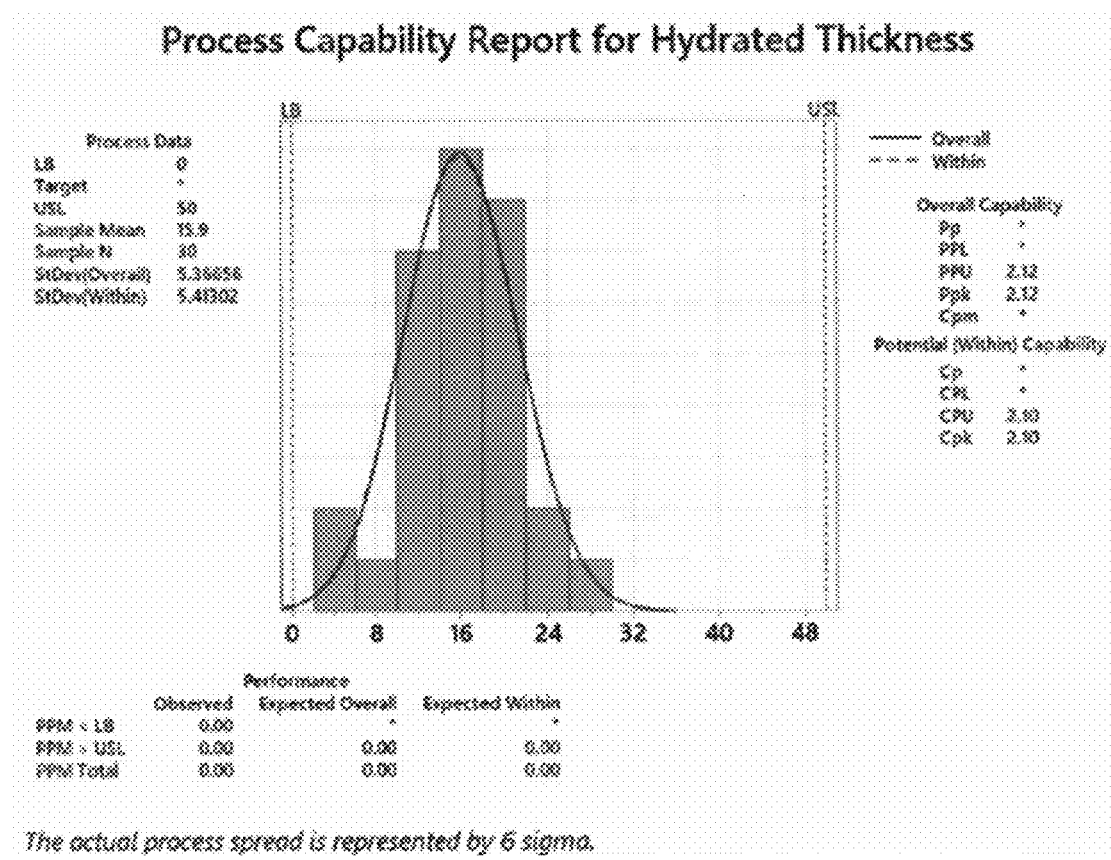
FIG. 7 is a process capability report for hydrated thickness for reprocessed single-use medical device validation.

FIG. 7 illustrates a process capability report for hydrated thickness showing process data, overall capability, potential capability, and performance.

Next friction testing was conducted for lubricity and durability of the coating on each of the reprocessed single-use medical devices. Acceptance criteria was lubricity less than or equal to 171 grams grand average force over a 15-pull test cycle. Frictional force produces a robust process capability having a $Pp_k$ of 26.38. Table 10 shows the parameters of the friction testing.

TABLE 10

Friction Testing Parameters

Friction Force Testing Parameters

| Instrument: | FTS Series |
| --- | --- |
| Fixtures: | Alligator clip |
| Friction Testing Pads: | 60A FTS Pads |
| Clamp Force Setting (grams): | 500 |
| Velocity (cm/second): | 1.0 |
| Acceleration Time (seconds): | 1.0 |
| Pull Distance (cm): | 10.0 |
| Cycles: | 15 |
| Sample Rate (sample/mm): | 1 |

Figure 8:
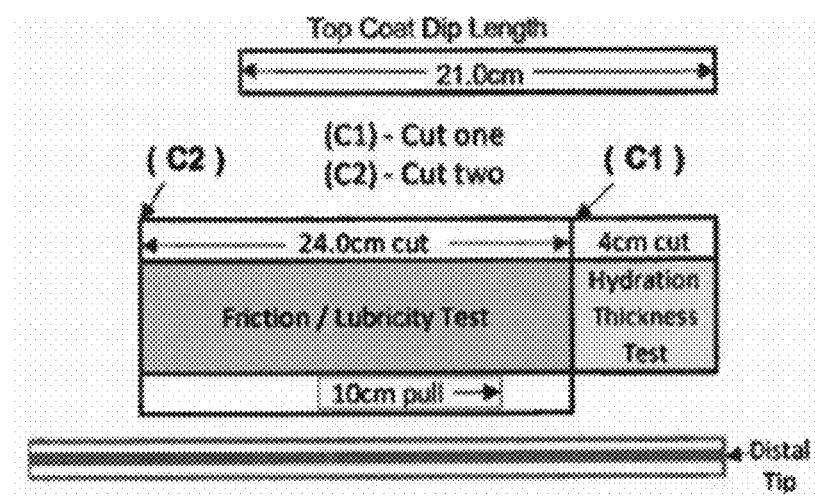
FIG. 8 is an actual friction/lubricity and hydrated coating thickness (µm) testing diagram.

FIG. 8 illustrates an actual friction/lubricity and hydrated coating thickness (μm) testing diagram. Table 11 illustrates friction testing summary statistics (for grand average friction force in grams).

TABLE 11

Friction Testing Summary Statistics

| Description | Value |
| --- | --- |
| Minimum, Maximum Value | 3.81, 12.64 |
| Mean | 7.256 |
| Standard Deviation | 0.498 |

Figure 9:
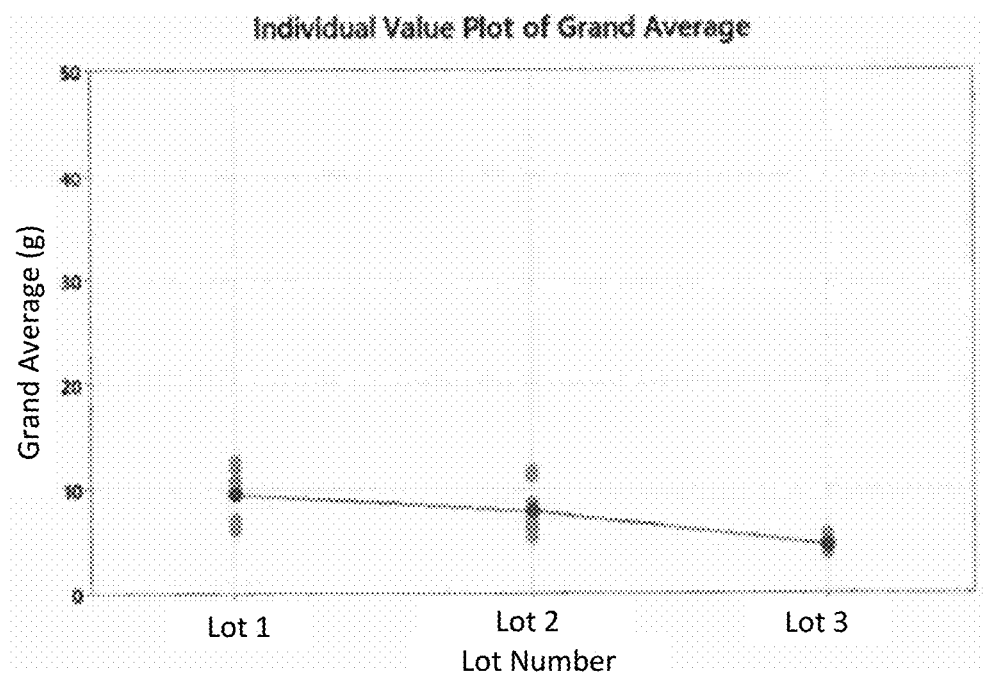
FIG. 9 is an individual value plot of grand average force for reprocessed single-use medical device validation.
Figure 10:
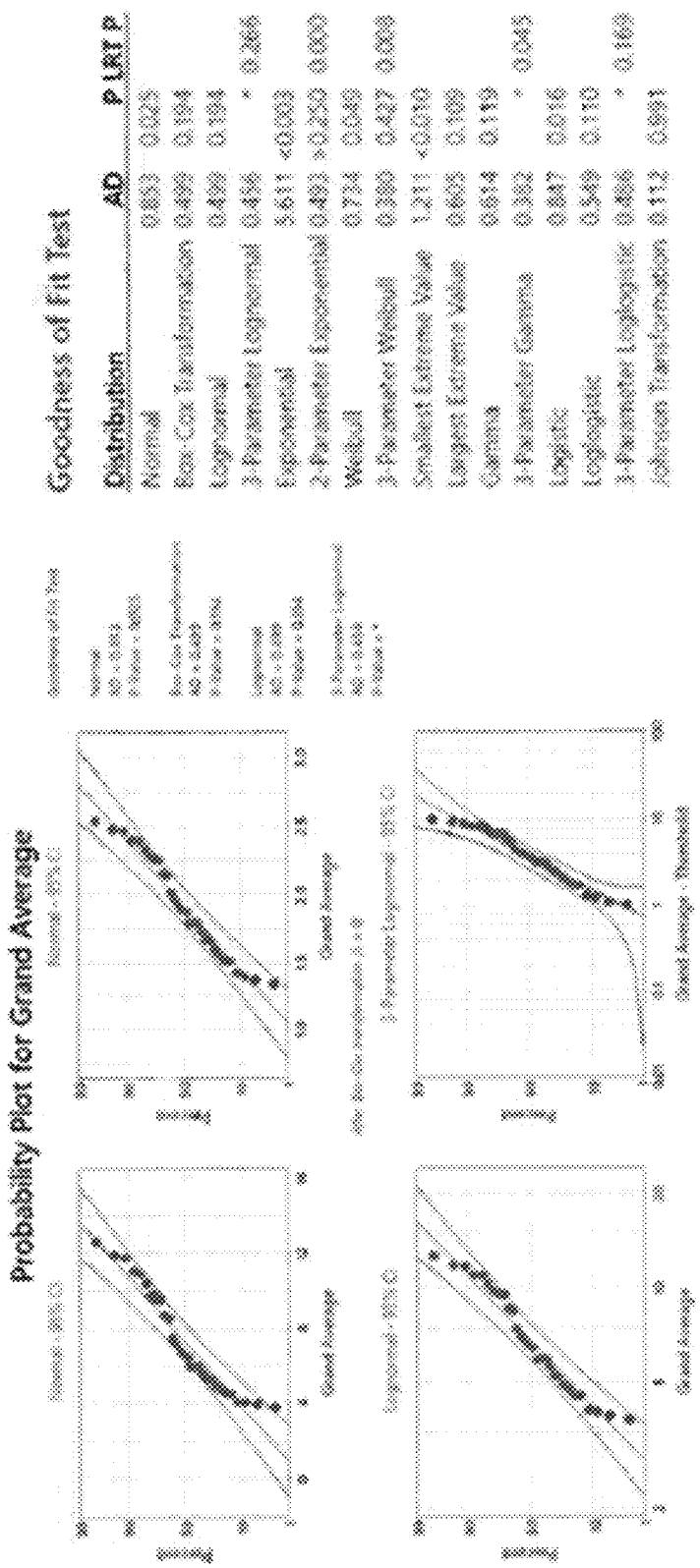
FIG. 10 is a lognormal goodness of fit test for reprocessed single-use medical device validation.
Figure 11:
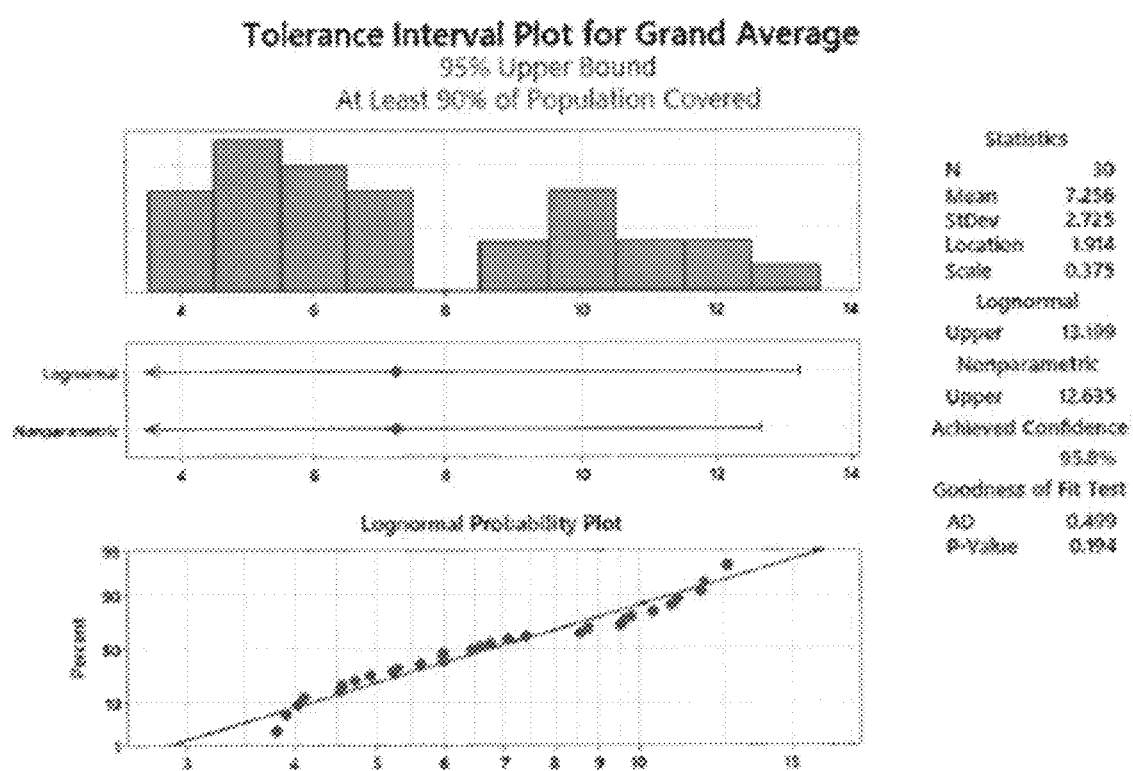
FIG. 11 is a tolerance interval plot for grand average force for reprocessed single-use medical device validation.
Figure 12:
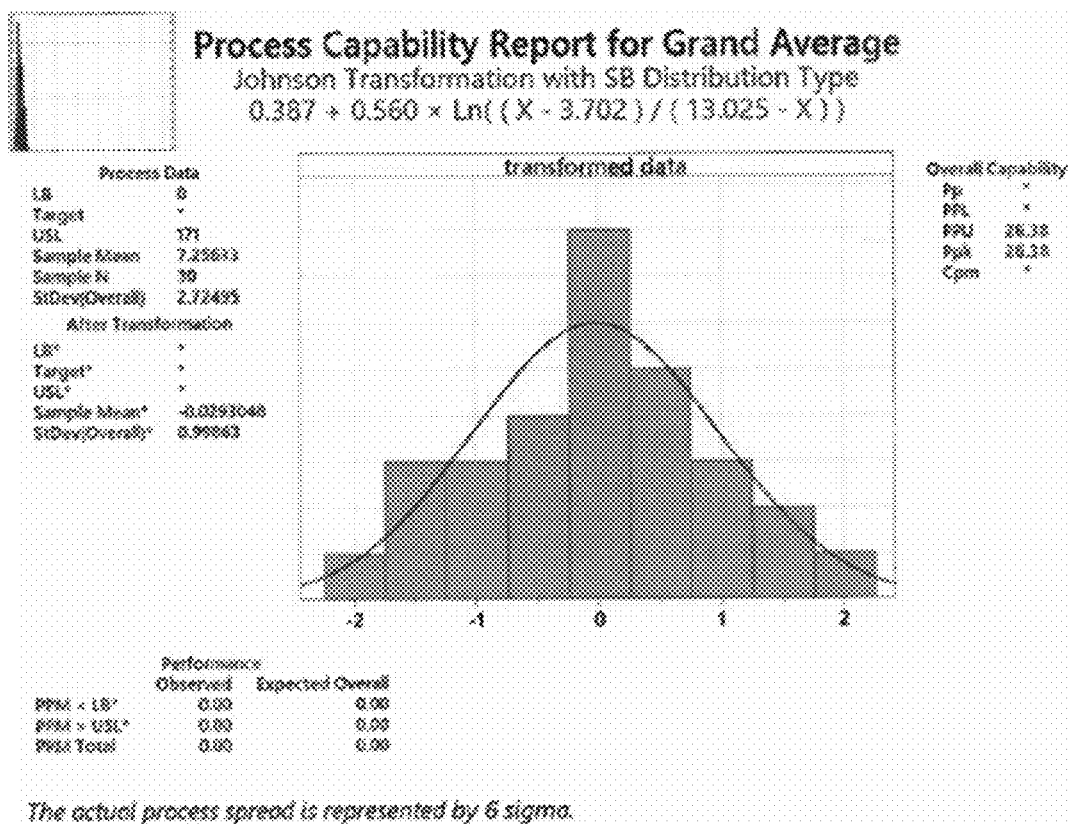
FIG. 12 is a process capability chart for grand average force for reprocessed single-use medical device validation.

FIG. 9 illustrates an individual box blot of grand average friction force (grams) for each tested single-use medical device. FIG. 10 illustrates goodness of fit lognormal plots for the grand average testing. FIG. 11 illustrates a tolerance interval plot for grand average having a mean of 7.256 grams, a standard deviation of 2.725 grams, a location of 1.914 cm, a scale of 0.375, an achieved confidence of 95.8%, a goodness of fit Ad value of 0.499 and a p-value of 0.194. FIG. 12 illustrates a process capability report for grand average with a Johnson transformation with SB distribution type.

As discussed, the reprocessed single-use medical devices have characteristics within the required tolerances (e.g., length, hydrated thickness, and grand average force). Therefore, using the removal method described herein allows for single-use coated medical devices to be reused by removing the coatings, cleaning the single-use medical device surface areas, and recoating the single-use medical devices.

Illustrative Aspects

Aspect 1: A method for reprocessing a single-use medical device comprising: removing, via a removal assembly, one or more coatings on the surface of the single-use medical device; validating that the one or more coatings have been completely removed from the surface of the single-use medical device; validating that a surface integrity of the single-use medical device is sufficient to apply one or more new coatings; and preparing the surface of the single-use medical device for the one or more new coatings.

Aspect 2: The method of aspect 1, wherein the method further comprises detecting, via a detection assembly, one or more coatings on a surface of the single-use medical device prior to removing the one or more coatings.

Aspect 3: The method of aspect 1, wherein the method further comprises applying the one or more new coatings to the surface of the single-use medical device.

Aspect 4: The method of aspect 3, wherein the method further comprises validating, via a detection assembly, that the one or more new coatings are properly applied to the single-use medical device.

Aspect 5: The method of aspect 2, wherein the detection assembly comprises one or more light sources configured to provide a light to the surface of the single-use medical device and a photodetector configured to receive a reflected light from the surface of the single-use medical device, wherein the photodetector is operable to determine a number of coatings on the single-use medical device and a length, width, thickness, location, and chemical composition of each coating based on the light received or lack of light received at the photodetector.

Aspect 6: The method of aspect 2, wherein the detection assembly comprises a dye applicator configured to apply a dye to the surface of the single-use medical device and a machine vision system, wherein the dye stains the one or more coatings on the singe-use medical device.

Aspect 7: The method of aspect 6, wherein the machine vision system is operable to determine a number, a length, a width, a thickness, and a chemical composition of the one or more coatings based on the dye staining the coating.

Aspect 8: The method of aspect 2, wherein the detection assembly comprises a fluid chamber containing a fluid, the fluid chamber operable to receive the single-use medical device and machine vision system or one or more proximity sensors, wherein the single-use medical device is exposed to the fluid in the fluid chamber, wherein exposing the single-use medical device to the fluid causes characteristics of the one or more coatings to change in comparison to one or more non-coated sections of the medical device.

Aspect 9: The method of aspect 8, wherein the machine vision system or the one or more proximity sensors are operable to determine a number, a length, a width, a thickness, and a chemical composition of the one or more coatings based on changes in the characteristics of the one or more coatings.

Aspect 10: The method of aspect 8, wherein the liquid chamber is a humidity chamber and the liquid is humid air.

Aspect 11: The method of aspect 2, wherein the detection assembly comprises a scanning electron microscope configured to determine a number, a length, a width, a thickness, and a chemical composition of the one or more coatings based on differences in surface characteristics of the single-use medical device for the one or more coatings and one or more non-coated sections.

Aspect 12: The method of aspect 2, wherein the detection assembly comprises a heating element operable to provide heat to the single-use medical device and a differential scanning calorimeter configured to determine a number, a length, a width, a thickness, and a chemical composition of the one or more coatings based on differences in heat flows between the one or more coatings and one or more non-coated sections.

Aspect 13: The method of aspect 2, the method further comprising choosing a desired removal assembly based on a number, a length, a width, a thickness, and a chemical composition of the one or more coatings.

Aspect 14: The method of aspect 13, wherein the removal assembly comprises an ultrasonic tank configured to contain a liquid and the single-use medical device and an ultrasound emitter configured to emit ultrasonic sound waves into the ultrasonic tank thereby causing cavitation of the liquid and removal of the one or more coatings from the single-use medical device by the cavitation of the liquid, wherein the liquid is contained in the ultrasonic tank at a temperature of about 50 degrees C. to about 90 degrees C.

Aspect 15: The method of aspect 13, wherein the removal assembly comprises a tank operable to contain the single-use medical device and one or more high pressure nozzles configured to provide a fluid on to the one or more coatings on the single-use medical device, wherein the one or more high pressure nozzles are configured to provide a fluid to the one or more coatings for a duration based on the thickness and chemical composition of the one or more coatings.

Aspect 16: The method of aspect 13, wherein the removal assembly comprises a tank operable to contain a solvent, the solvent configured to breakdown the one or more coatings on the single-use medical device, wherein the one or more coatings can be removed by wiping the one or more coatings from the surface of the single-use medical device after the one or more coatings have been broken down by the solvent.

Aspect 17: The method of aspect 16, wherein the solvent is one or more of denatured ethyl alcohol, a baking soda solution, or other solvents configured to break bounds between a polymer in the coating and a solvent used to make the coating.

Aspect 18: The method of aspect 13, wherein the removal assembly comprises a tank operable to contain the single-use medical device and one or more bead blasting nozzles configured to provide a plurality of beads to the one or more coatings, thereby removing the coatings, wherein the plurality of beads comprise one or more of crushed/formed dry ice ($CO_2$) or other materials.

Aspect 19: The method of aspect 13, wherein the removal assembly comprises a tank operable to contain the single-use medical device and an electrostatic charge emitter operable to emit an electrostatic charge to the one or more coatings causing the one or more coatings to be repelled from the surface of the single-use medical device thereby removing the one or more coatings from the single use medical device.

Aspect 20: The method of aspect 19, wherein the electrostatic charge charges the polarity of the one or more coatings thereby repelling the one or more coatings from the surface of the single-use medical device.

Aspect 21: The method of aspect 13, wherein the removal assembly comprises a tank operable to contain the single-use medical device and a fluid provider configured to provide an acidic chemical or an alkaline chemical to the tank, wherein the acidic or the alkaline chemical is chosen based on the chemical composition of the one or more coatings, wherein the acidic chemical or the alkaline chemical react with the one or more coatings thereby stripping the one or more coatings from the surface of the single-use medical device.

Aspect 21: The method of aspect 13, wherein the removal assembly comprises a tank configured to contain the single-use medical device and a heating element or a cooling element configured to provide a temperature to the interior of the tank, wherein the temperature provided to the tank dries, freezes, or melts the one or more coatings, thereby allowing the one or more coatings to be easily removed from the surface of the single-use medical device.

Aspect 22: The method of aspect 13, wherein heating element provides a temperature sufficient to melt the one or more coatings off of the surface of the single-use medical device.

Aspect 23: The method of aspect 22, wherein the temperature is about 150 degrees C. to about 180 degrees C., or more.

Aspect 24: The method of aspect 13, wherein the removal assembly comprises a vacuum chamber operable to dehydrate the one or more coatings on the single-use medical device thereby allowing the one or more coatings to be easily removed from the surface of the single-use medical device.

Aspect 25: A method for reprocessing a single-use medical device comprising: removing one or more coatings on the surface of the single-use medical device; validating the surface of the single-use medical device for the coating removal; and preparing the surface of the single-use medical device to form a prepared surface on the single-use medical device.

Aspect 26: The method of aspect 25, the method further comprising detecting the one or more coatings on the surface of the single-use medical device prior to removing the one or more coatings.

Aspect 27: The method of aspect 26, wherein detecting the one or more coatings comprises detecting a length, width, thickness, mass, geometry, and chemical composition of the one or more coatings.

Aspect 28: The method of aspect 25, the method further comprising applying one or more new coatings on the prepared surface of the single-use medical device and validating the one or more new coatings on the single-use medical device.

Aspect 29: The method of aspect 26, wherein the one or more coatings is a polymeric coating.

Aspect 30: The method of aspect 29, wherein the polymeric coating is a single polymeric coating, two polymeric coatings, or more than two polymeric coatings.

Aspect 31: The method of aspect 29, wherein the polymeric coating comprises a hydrophobic polymeric coating, a hydrophilic polymeric coating, an amphiphilic coating, or a combination thereof.

Aspect 32: The method of aspect 31, wherein the polymer coating is a hydrophilic polymeric coating.

Aspect 33: The method of aspect 25, wherein the one or more coatings have a thickness from about 5.0 µm to about 250 µm.

Aspect 34: The method of aspect 25, wherein validating the surface of the single-use medical device for coating removal comprises detecting a presence or an absence of a residual coating on the surface of the single-use medical device.

Aspect 35: The method of aspect 34, wherein when the presence of the residual coating on the surface of the single-use medical device is detected the single-use medical device undergoes removing the one or more coatings for a second time.

Aspect 36: The method of aspect 25, wherein the method meets FDA requirements and industrial standards.

Aspect 37: The method of aspect 2, wherein detecting the one or more coatings on the single-use medical device comprises utilizing a light assembly, a fluid assembly, magnification, a dye assembly, an artificial intelligence method, a scanning electron microscope assembly, a differential scanning calorimetry assembly, or a combination thereof.

Aspect 38: The method of aspect 1, wherein removing the one or more coatings from the single-use medical device comprises utilizing a mechanical removal assembly, a chemical removal assembly, an environmental removal assembly, or a combination thereof.

Aspect 39: The method of aspect 38, wherein the mechanical removal assembly is an ultrasonic assembly, a high-pressure water jet assembly, a solvent wiping assembly, bead blasting assembly, laser removal assembly, or a combination thereof.

Aspect 40: The method of aspect 38, wherein the chemical method comprises electrostatic removal assembly, an acidic removal assembly, or a basic removal assembly.

Aspect 41: The method of aspect 38, wherein the environmental method comprises a heat method, a freeze method, or a vacuum method.

Aspect 42: The method of aspect 25, wherein preparing the surface of the single-use medical device comprises cleaning the surface, rinsing the surface with a polar solvent, and drying the surface of the single-use medical device.

Aspect 43: The method of aspect 42, wherein the drying step is conducted from about 50° C. to about 150° C.

Aspect 44: The method of aspect 32, wherein removing the one or more coatings from the single-use medical device comprises exposing the one or more coatings to denatured ethyl alcohol.

Aspect 45. A method for reprocessing a single-use medical device comprising: removing one or more coatings on a surface of the single-use medical device by contacting the one or more coatings on the surface of a single-use medical device to denatured ethyl alcohol, wherein the denatured ethyl alcohol completely removes the one or more coatings; validating the surface of the single-use medical device for the coating removal by visually inspecting the single-use medical device for any residual coating or using other detection methods; and preparing the surface of the single-use medical device for coating to form a prepared surface on the single-use medical device.

Aspect 46. The method of aspect 45, wherein preparing the surface of the single-use medical device comprises: placing the single-use medical device in an ultrasonic tank containing about 2 gallons to about 4 gallons of hydrogen peroxide; emitting an ultrasonic frequency within the ultrasonic tank of about 20 Hz to about 40 Hz for about 5 minutes to about 30 minutes; removing the single-use medical device from the ultrasonic tank; placing the single-use medical device in an exposure tank containing about 2 gallons to about 4 gallons of hydrogen peroxide; soaking the single-use medical device in hydrogen peroxide for about 5 minutes to about 30 minutes; flushing the exposure tank; removing the single-use medical device from the exposure tank; placing the single-use medical device in a rinse tank; rinsing the single-use medical device with water provided by a pump in fluid communication with the rinse tank at a flow rate of about 3 gal/min to about 4 gal/min for about 1 minute to about 30 minutes; and drying the single-use medical device.

Aspect 47. The method of aspect 46, wherein exposing the one or more coatings to denatured ethyl alcohol comprises wiping the one or more coatings five times with a polyester wipe containing denatured ethyl alcohol.

Aspect 48. The method of aspect 46, wherein exposing the one or more coatings to denatured ethyl alcohol comprises soaking the single-use medical device in a tank filled with denatured ethyl alcohol for about 5 minutes to about 1 hour and then wiping the one or more coatings off the surface of the single-use medical device using a polyester wipe or rag.

Aspect 49. The method of aspect 46, wherein the denatured ethyl alcohol is a solution comprising 99% denatured ethyl alcohol.

Aspect 50. The method of aspect 46, wherein validating the surface of the single-use medical device for the coating removal further comprises a light detection method, a fluid detection method, a magnification method, a dye method, an artificial intelligence method, a scanning electron microscope method, a differential scanning calorimetry method, or any combination thereof.

Aspect 51. The method of aspect 46, wherein the one or more coatings comprise hydrophilic coatings.

Aspect 52. The method of aspect 46, wherein the method further comprises wiping a luer and a strain relief the single-use medical device with a polyester wipe containing 3% hydrogen peroxide solution after removing the single-use medical device from the ultrasonic tank.

Aspect 53. The method of aspect 47, wherein the exposure tank is maintained a pressure of about 45 psi.

Aspect 54. The method of aspect 47, wherein the water used to rinse the single-use medical device has a temperature of about 15 degrees C. to about 30 degrees C.

Aspect 55. The method of aspect 47, wherein drying the single-use medical device comprises applying a temperature of about 50 degrees C. to about 150 degrees C.

Aspect 56. The method of aspect 47, wherein drying the single-use medical device comprises wiping the single-use medical device 10 times with a dry polyester wipe.

Aspect 57. The method of aspect 47, the method further comprising validating the prepared surface using visual inspection to ensure the prepared surface is ready for a new coating to be applied.

Aspect 58. The method of aspect 57, the method further comprising sterilizing the single-use medical device.

Aspect 59. The method of claim 1, the method further comprising applying one or more new coatings to the single-use medical device; and validating the one or more new coatings on the single-use medical device.

Aspect 60. The method of aspect 46, wherein removing the one or more coatings further comprises mechanically removing the one or more coatings, chemically removing the one or more coatings, environmentally removing the one or more coatings, or any combination thereof.

Aspect 61. The method of aspect 60, wherein mechanically removing the one or more coatings comprises an ultrasonic removal method, a high-pressure water jet removal method, a bead blasting method, a laser removal method, or a combination thereof.

Aspect 62. The method of aspect 60, wherein chemically removing the one or more coatings comprises providing an electrostatic charge to the one or more coatings, providing an acidic solution to the one or more coatings, providing a basic solution to the one or more coatings, or combinations thereof.

Aspect 63. The method of aspect 60, wherein environmentally removing the one or more coatings comprises heating the one or more coatings to a temperature above a melting point of the one or more coatings, cooling the one or more coatings to freeze the one or more coatings, or placing the one or more coatings in a vacuum chamber.

Aspect 64. The method of aspect 46, wherein the one or more coatings have a thickness of about 5.0 µm to about 250 µm.

Aspect 65. The method of aspect 46, wherein the single-use medical device has been used in a patient prior to removing the one or more coatings.

The disclosures shown and described above are only examples. Even though numerous characteristics and advantages of the present technology have been set forth in the foregoing description, together with details of the structure and function of the present disclosure, the disclosure is illustrative only, and changes may be made in the detail, especially in matters of shape, size and arrangement of the parts within the principles of the present disclosure to the full extent indicated by the broad general meaning of the terms used in the attached claims. It will therefore be appreciated that the examples described above may be modified within the scope of the appended claims. The method steps provided herein can be performed in various orders. Some method steps can be performed before or after others although not stated in this disclosure.

What is claimed is:

1. A method for reprocessing a single-use medical device comprising:
    a) removing one or more coatings on a surface of the single-use medical device by contacting the one or more coatings on the surface of a single-use medical device to denatured ethyl alcohol, wherein the denatured ethyl alcohol removes the one or more coatings;
    b) validating the surface of the single-use medical device for the coating removal by visually inspecting the single-use medical device for any residual coating or using other detection methods; and
    c) preparing the surface of the single-use medical device for coating to form a prepared surface on the single-use medical device, wherein preparing the surface of the single-use medical device comprises:
        i. contacting the single-use medical device to a hydrogen peroxide solution or an enzymatic solution;
        ii. rinsing the single-use medical device with water; and
        iii. drying the single-use medical device.

2. The method of claim 1, wherein an ultrasonic frequency is provided to the single-use medical device contacting the hydrogen peroxide solution or enzymatic solution.

3. The method of claim 2, wherein the ultrasonic frequency is provided for about 5 minutes to about 30 minutes at a frequency of about 20 Hz to about 40 Hz.

4. The method of claim 1, wherein contacting the one or more coatings with denatured ethyl alcohol comprises wiping the one or more coatings seven times with a polyester wipe containing denatured ethyl alcohol.

5. The method of claim 1, wherein contacting the one or more coatings with denatured ethyl alcohol comprises soaking the single-use medical device in a tank filled with denatured ethyl alcohol for about 5 minutes to about 1 hour and then wiping the one or more coatings off the surface of the single-use medical device using a polyester wipe or rag.

6. The method of claim 1, wherein validating the surface of the single-use medical device for the coating removal further comprises a light detection method, a fluid detection method, a magnification method, a dye method, an artificial intelligence method, a scanning electron microscope method, a differential scanning calorimetry method, or any combination thereof.

7. The method of claim 1, wherein the one or more coatings comprise hydrophilic coatings.

8. The method of claim 1, wherein the method further comprises wiping a luer and a strain relief the single-use medical device with a polyester wipe containing 3% hydrogen peroxide solution.

9. The method of claim 1, wherein the water used to rinse the single-use medical device has a temperature of about 15 degrees C. to about 30 degrees C.

10. The method of claim 1, wherein drying the single-use medical device comprises applying a temperature of about 50 degrees C. to about 150 degrees C.

11. The method of claim 1, wherein drying the single-use medical device comprises wiping the single-use medical device 10 times with a dry polyester wipe.

12. The method of claim 1, the method further comprising validating the prepared surface using visual inspection to ensure the prepared surface is ready for a new coating to be applied.

13. The method of claim 12, the method further comprising sterilizing the single-use medical device.

14. The method of claim 1, the method further comprising:
a) applying one or more new coatings to the single-use medical device; and
b) validating the one or more new coatings on the single-use medical device.

15. The method of claim 1, wherein removing the one or more coatings further comprises mechanically removing the one or more coatings, chemically removing the one or more coatings, environmentally removing the one or more coatings, or any combination thereof.

16. The method of claim 15, wherein mechanically removing the one or more coatings comprises an ultrasonic removal method, a high-pressure water jet removal method, a bead blasting method, a laser removal method, or a combination thereof.

17. The method of claim 15, wherein chemically removing the one or more coatings comprises providing an electrostatic charge to the one or more coatings, providing an acidic solution to the one or more coatings, providing a basic solution to the one or more coatings, or combinations thereof.

18. The method of claim 15, wherein environmentally removing the one or more coatings comprises heating the one or more coatings to a temperature above a melting point of the one or more coatings, cooling the one or more coatings to freeze the one or more coatings, or placing the one or more coatings in a vacuum chamber.

19. The method of claim 1, wherein the one or more coatings have a thickness of about 5.0 μm to about 250 μm.

20. The method of claim 1, wherein the single-use medical device has been used in a patient prior to removing the one or more coatings.

* * * * *